United States Patent
Siebel et al.

(10) Patent No.: US 11,266,431 B2
(45) Date of Patent: Mar. 8, 2022

(54) ULTRASONIC SURGICAL INSTRUMENT WITH SLIDING BLADE SHEATH

(71) Applicant: Ethicon LLC, Guaynabo, PR (US)

(72) Inventors: Tony C. Siebel, Cincinnati, OH (US); William B. Weisenburgh, II, Maineville, OH (US); Jeffrey D. Messerly, Cincinnati, OH (US); Matthew C. Miller, Cincinnati, OH (US); Cory G. Kimball, Hamilton, OH (US)

(73) Assignee: Cilag GmbH International, Zug (CH)

( * ) Notice: Subject to any disclaimer, the term of this patent is extended or adjusted under 35 U.S.C. 154(b) by 199 days.

(21) Appl. No.: 16/380,238

(22) Filed: Apr. 10, 2019

(65) Prior Publication Data

US 2019/0298405 A1    Oct. 3, 2019

Related U.S. Application Data

(63) Continuation of application No. 15/097,630, filed on Apr. 13, 2016, now Pat. No. 10,433,864.

(51) Int. Cl.
*A61B 17/32* (2006.01)
*A61B 17/28* (2006.01)
(Continued)

(52) U.S. Cl.
CPC .. *A61B 17/320092* (2013.01); *A61B 17/2812* (2013.01); *A61B 17/2841* (2013.01);
(Continued)

(58) Field of Classification Search
CPC .. A61B 17/320092; A61B 2017/00017; A61B 2017/00207; A61B 2017/00367;
(Continued)

(56) References Cited

U.S. PATENT DOCUMENTS 200,754 A    2/1878  Pichon
2,846,766 A    8/1958  Harter
(Continued)

FOREIGN PATENT DOCUMENTS

CN    103442658 A    12/2013
EP     2394591 A1    12/2011
(Continued)

OTHER PUBLICATIONS

European Communication dated Sep. 27, 2019 for Application No. 17718259.9, 5 pages.
(Continued)

*Primary Examiner* — George J Ulsh
(74) *Attorney, Agent, or Firm* — Frost Brown Todd LLC

(57) ABSTRACT

A surgical instrument includes a gripping assembly, a shaft assembly, an end effector, and a pivoting member. The gripping assembly defines a first opening for receiving a finger or a thumb of a user. The gripping assembly includes a first deformable feature that is configured to be moved in order to increase or decrease a cross-sectional area of the first opening. The shaft assembly extends distally from the gripping assembly. The end effector is positioned at a distal end of the shaft assembly and includes a first member. The pivoting member is pivotably coupled with the shaft assembly. The pivoting member is pivotable with respect to the first member of the end effector between an open position and a closed position to thereby clamp tissue between the first member and the pivoting member.

18 Claims, 20 Drawing Sheets

(51) Int. Cl.
*A61B 17/3201* (2006.01)
*A61B 17/00* (2006.01)
*A61B 17/29* (2006.01)

(52) U.S. Cl.
CPC .............................. *A61B 17/3201* (2013.01); *A61B 2017/00017* (2013.01); *A61B 2017/0042* (2013.01); *A61B 2017/00207* (2013.01); *A61B 2017/00367* (2013.01); *A61B 2017/00424* (2013.01); *A61B 2017/00858* (2013.01); *A61B 2017/00946* (2013.01); *A61B 2017/2911* (2013.01); *A61B 2017/320044* (2013.01); *A61B 2017/320078* (2017.08); *A61B 2017/320094* (2017.08); *A61B 2017/320095* (2017.08)

(58) Field of Classification Search
CPC .. A61B 2018/0042; A61B 2017/00424; A61B 2017/00858; A61B 2017/00946; A61B 2017/2911; A61B 2017/320044; A61B 2017/320078; A61B 17/2812; A61B 17/3201
See application file for complete search history.

(56) References Cited

U.S. PATENT DOCUMENTS

| | | | |
|---|---|---|---|
| 5,322,055 A | 6/1994 | Davison et al. | |
| 5,873,873 A | 2/1999 | Smith et al. | |
| 5,980,510 A | 11/1999 | Tsonton et al. | |
| 6,325,811 B1 | 12/2001 | Messerly | |
| 6,773,444 B2 | 8/2004 | Messerly | |
| 6,783,524 B2 | 8/2004 | Anderson et al. | |
| 7,063,692 B2 | 6/2006 | Sakurai et al. | |
| 8,460,337 B2 | 6/2013 | Shelton, Iv et al. | |
| 8,461,744 B2 | 6/2013 | Wiener et al. | |
| 8,523,889 B2 | 9/2013 | Stulen et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,986,302 B2 | 3/2015 | Aldridge et al. | |
| 9,023,071 B2 | 5/2015 | Miller et al. | |
| 9,107,688 B2 | 8/2015 | Kimball et al. | |
| 9,339,289 B2 | 5/2016 | Robertson | |
| 9,381,058 B2 | 7/2016 | Houser et al. | |
| 10,433,864 B2 | 10/2019 | Siebel et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2008/0234710 A1 | 9/2008 | Neurohr et al. | |
| 2012/0116265 A1 | 5/2012 | Houser et al. | |
| 2012/0174415 A1 | 7/2012 | Sataloff | |
| 2013/0324991 A1* | 12/2013 | Clem .............. A61B 17/320068 606/33 |
| 2014/0207163 A1 | 7/2014 | Eichmann et al. | |
| 2015/0080923 A1 | 3/2015 | Kojima et al. | |
| 2015/0080925 A1 | 3/2015 | Schulte et al. | |
| 2015/0141981 A1 | 5/2015 | Price et al. | |
| 2015/0148833 A1 | 5/2015 | Stokes et al. | |
| 2017/0172594 A1* | 6/2017 | Allen, IV .............. A61B 17/295 |

FOREIGN PATENT DOCUMENTS

| | | |
|---|---|---|
| EP | 2641550 A2 | 9/2013 |
| JP | S55-143169 U | 10/1980 |
| JP | S63-098175 U | 6/1988 |
| JP | 2001-314411 A | 11/2001 |
| JP | 2003-038869 A | 2/2003 |
| JP | 2008-508065 A | 3/2008 |
| JP | 2009-195451 A | 9/2009 |
| JP | 2010-522034 A | 7/2010 |
| JP | 2013-085761 A | 5/2013 |
| WO | WO 2016/163450 A1 | 10/2016 |

OTHER PUBLICATIONS

International Search Report and Written Opinion dated Sep. 4, 2017 for International Application No. PCT/US2017/025960, 17 pages.
U.S. Appl. No. 61/410,603, filed Nov. 5, 2010.
Non-Provisional U.S. Appl. No. 17/410,368.
U.S. Pat. No. 10,433,864.
Chinese Office Action, and First Search dated Jan. 19, 2021 for Application No. CN 201780023596.9, 15 pgs.
European Search Report and Written Opinion dated Nov. 24, 2020 for Application No. EP 20193933.7, 11 pgs.
European Search Report and Written Opinion dated Nov. 25, 2020 for Application No. EP 20193954.3, 8 pgs.
Japanese Office Action, Notice of Reasons for Refusal and Search Report by Registered Search Organization, dated Apr. 13, 2021 for Application No. JP 2018-554041, 23 pgs.

* cited by examiner

ULTRASONIC SURGICAL INSTRUMENT WITH SLIDING BLADE SHEATH

This application is a continuation of U.S. patent application Ser. No. 15/097,630, entitled "Ultrasonic Surgical Instrument with Sliding Blade Sheath," filed Apr. 13, 2016, issued as U.S. Pat. No. 10,433,864 on Oct. 8, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the surgeon's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008 now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012 now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
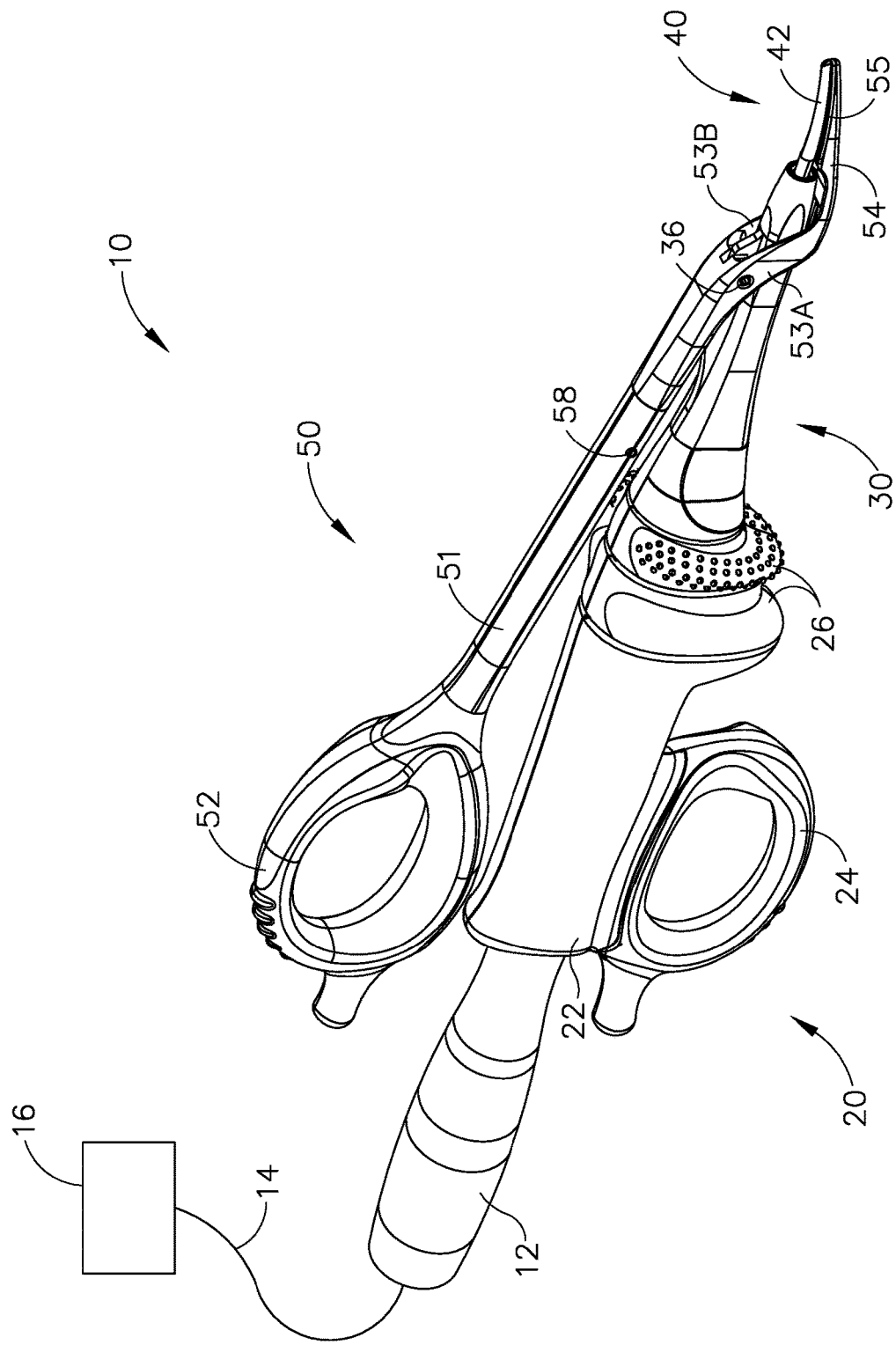
FIG. 1 depicts a perspective view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a finger grip (24) and a pair of buttons (26). Instrument (10) also includes a clamp arm assembly (50) that is pivotable toward and away from body (22). A proximal portion of clamp arm assembly (50) comprises a thumb grip (52). Thumb grip (52) and finger grip (24) together provide a scissor grip type of configuration. It should be understood, however, that various other suitable configurations may be used, including but not limited to a pistol grip configuration.

Figure 3:
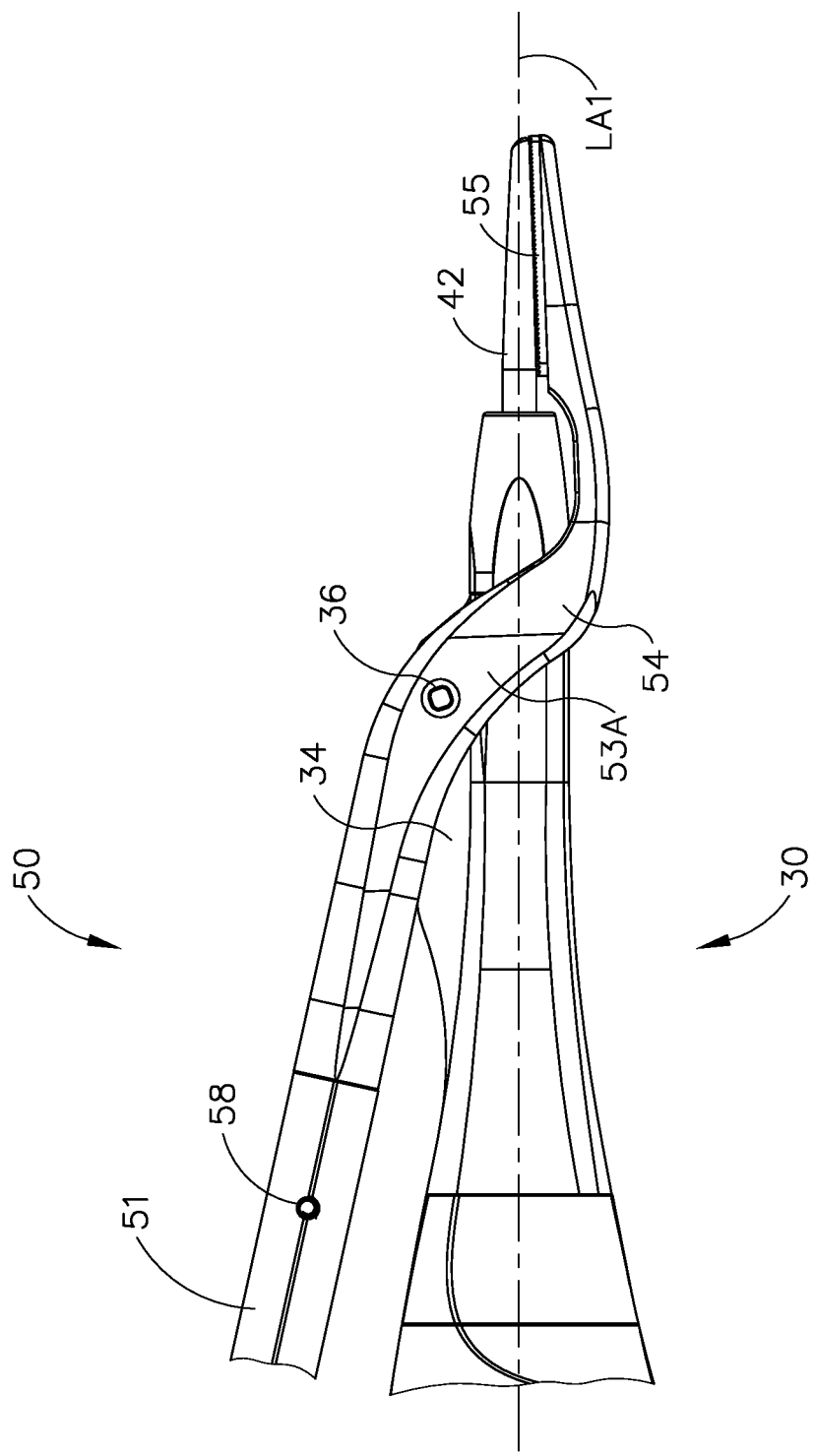
FIG. 3 depicts a side elevational view of the distal end of the instrument of FIG. 1.

End effector (40) includes an ultrasonic blade (42) extending distally from shaft assembly (30); and a pivoting clamp arm (54), which is an integral feature of clamp arm assembly (50). Clamp arm assembly (50) is pivotably coupled to a projection (34) extending laterally from shaft assembly (30) via a pivot member (36) (e.g., a pin, bearing, shaft, etc.) such that clamp arm (54) is pivotable toward and away from ultrasonic blade (42) to thereby clamp tissue between a clamp pad (55) of clamp arm (54) and ultrasonic blade (42). As best seen in FIG. 3, clamp arm assembly (50) is pivotably coupled to projection (34) such that clamp arm assembly (50) pivots about an axis that is offset from a longitudinal axis (LA1). It should be understood that such rotation about an offset axis may allow for a narrower shaft assembly (30) profile. It should be understood that shaft assembly (30)

passes through a portion of clamp arm assembly (50) such that as clamp arm assembly (50) rotates, clamp arm (54) rotates about a portion of shaft assembly (30). In particular, a first member (53A) and a second member (53B) of clamp arm assembly (50) are disposed about a distal portion of shaft assembly (30).

Figure 2:
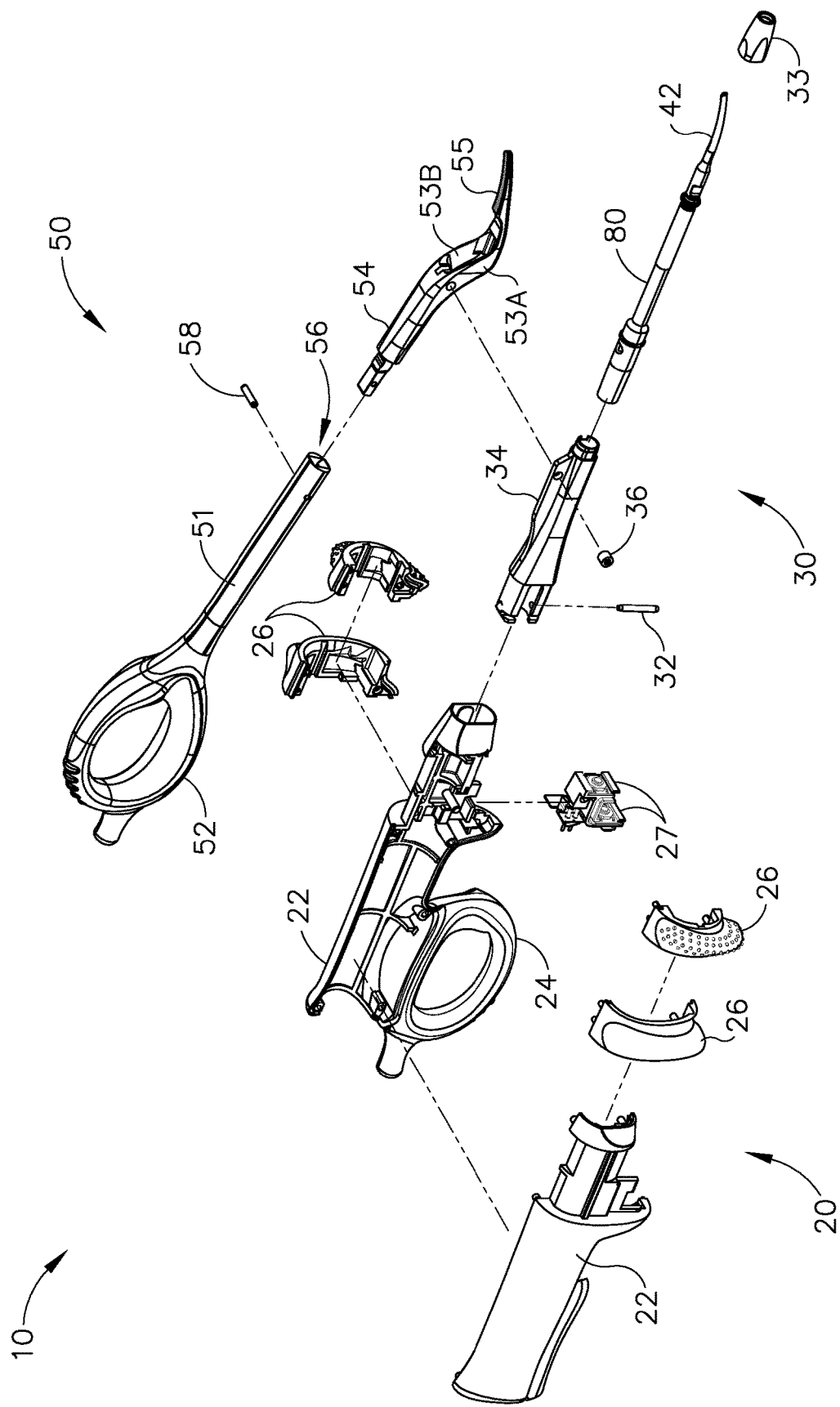
FIG. 2 depicts an exploded perspective view of the instrument FIG. 1.

Clamp arm assembly (50) is configured such that clamp arm (54) is pivotable toward ultrasonic blade (42) in response to pivoting of thumb grip (52) of clamp arm assembly (50) toward body (22); and such that clamp arm (54) is pivotable away from ultrasonic blade (42) in response to pivoting of thumb grip (52) of clamp arm assembly (50) away from body (22). As best seen in FIG. 2, a proximal end of clamp arm (54) is disposed within a distal recess (56) of a shank portion (51) of clamp arm assembly (50); and is secured therein by a pin (58). Various other suitable ways in which clamp arm (54) may be integrated into clamp arm assembly (50) will be apparent to those of ordinary skill in the art in view of the teachings herein. In some versions, one or more resilient members are used to bias clamp arm (54) and/or trigger (28) to an open position. By way of example only, such a resilient member may comprise a leaf spring, a torsion spring, and/or any other suitable kind of resilient member.

Figure 4:
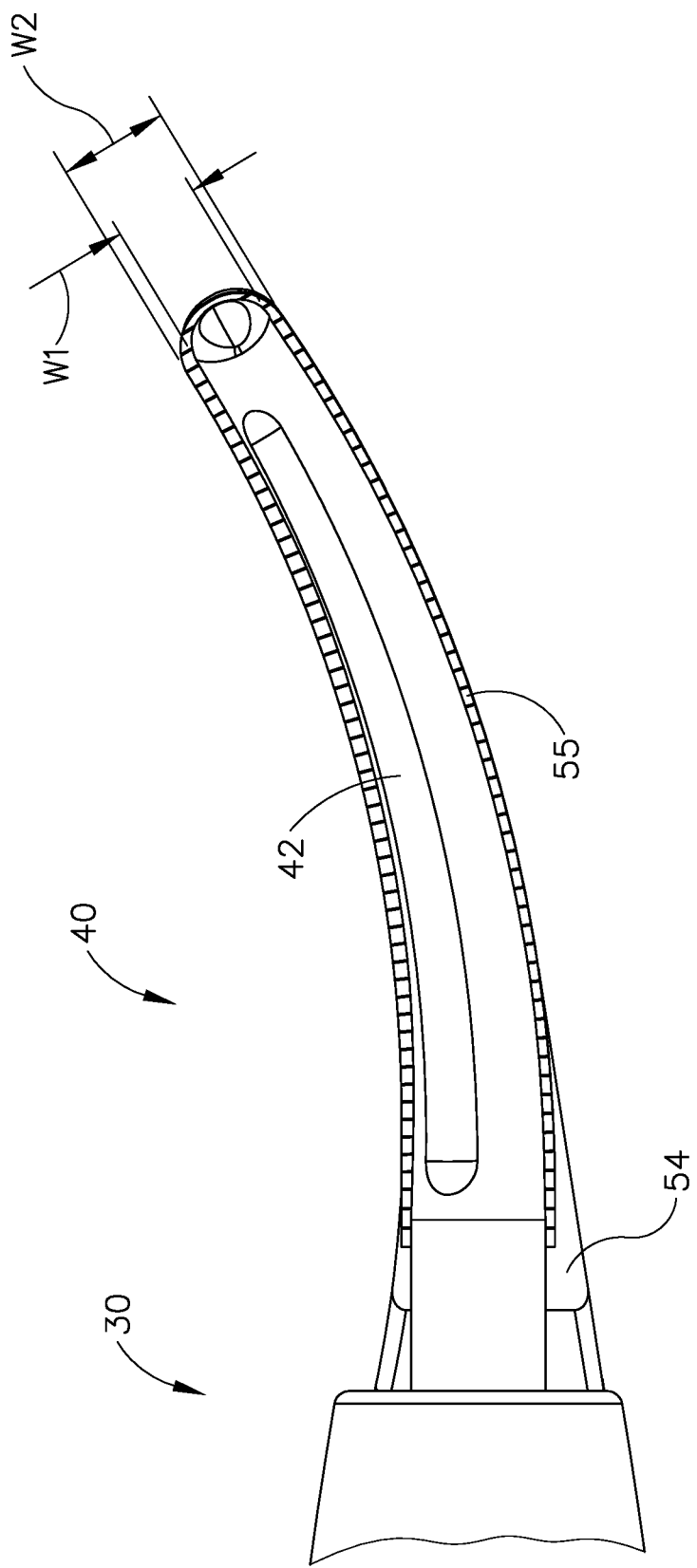
FIG. 4 depicts a top plan view of an end effector of the instrument of FIG. 1.

FIG. 4 shows a top view of end effector (40). The distal end of ultrasonic blade (42) has a width (W1). The distal end of clamp arm (54) has a width (W2). In the present example, the width (W2) of clamp arm (54) is greater than the width (W1) of ultrasonic blade (42). In some other versions, the width (W1) of ultrasonic blade (42) is greater than the width (W2) of clamp arm (54). In still other versions, the width (W1) of ultrasonic blade (42) is equal to the width (W2) of clamp arm (54). By way of further example only, end effector (40) may be constructed and operable in accordance with at least some of the teachings of U.S. Pub. No. 2015/0080925, entitled "Alignment Features for Ultrasonic Surgical Instrument," published Mar. 19, 2015, now abandoned, the disclosure of which is incorporated herein by reference, in its entirety.

As shown in FIG. 1, an ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN04, GEN11, or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (80), which extends through shaft assembly (30) to reach ultrasonic blade (42) as shown in FIG. 2. Waveguide (80) is secured within shaft assembly (30) via a pin (32), which passes through waveguide (80) and shaft assembly (30). Pin (32) is located at a position along the length of waveguide (80) corresponding to a node associated with resonant ultrasonic vibrations communicated through waveguide (80). As noted above, when ultrasonic blade (42) is in an activated state (i.e., vibrating ultrasonically), ultrasonic blade (42) is operable to effectively cut through and seal tissue, particularly when the tissue is being clamped between clamp arm (54) and ultrasonic blade (42).

In the present example, the distal end of ultrasonic blade (42) is located at a position corresponding to an anti-node associated with resonant ultrasonic vibrations communicated through waveguide (80), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (42), thereby providing oscillation of ultrasonic blade (42) at the resonant ultrasonic frequency. Thus, when tissue is secured between ultrasonic blade (42) and clamp arm (54), the ultrasonic oscillation of ultrasonic blade (42) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein. Other suitable configurations for end effector (40) will be apparent to those of ordinary skill in the art in view of the teachings herein.

An operator may activate buttons (26) to selectively close switches (27) (see FIG. 2), thereby selectively activating transducer assembly (12) to activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb in the ring formed by thumb grip (52), position their middle or ring finger in the ring formed by finger grip (24), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the references cited herein. Additional merely illustrative variations for instrument (10) will be described in greater detail below. It should be understood that the below described variations may be readily applied to instrument (10) described above and any of the instruments referred to in any of the references that are cited herein, among others.

II. Exemplary Alternative Ultrasonic Surgical Instrument Including Blunt Dissection and Adjustable Handle Features As discussed above, end effector (40) is operable to transect and seal tissue (or just seal tissue) by compressing the tissue between clamp pad (55) of clamp arm (54) and ultrasonic blade (42), while activating blade (42) with ultrasonic energy. It may be desirable to provide the end effector (40) with features that facilitate the use of end effector (40) in performing blunt dissections (e.g., by selectively increasing the effective width of end effector (40), by providing surface features to end effector (40) that enhance tissue gripping, etc.), in addition to allowing end effector (40) to also be used to transect and seal tissue ultrasonically. By way of example only, such versatility may be desirable in thoracic surgical procedures where the pulmonary artery, pulmonary vein, and/or bronchus need to be transected.

Furthermore, while instrument (10) is suitable for use by operators having differently sized hands, it may be desirable in some instances to allow an operator to customize or adjust aspects of instrument (10). For example, it may be desirable to provide adjustable features on handle assembly (20) to accommodate the operator's comfort in grasping instrument (10) and/or to improve overall ergonomics of instrument (10). Similarly, it may be desirable to provide gripping features on handle assembly (20) that facilitate grasping of instrument (10) using two or more different kinds of gripping styles.

The following description relates to examples of instrument (10) that include end effector (40) variations and handle assembly (20) variations that may provide the above-noted enhanced functionality. Other variations will be apparent to those of ordinary skill in the art in view of the teachings herein. It should be understood that the following teachings may be readily incorporated into instrument (10), such that structural and functional details that are omitted from the following discussion may simply be provided in accordance with the above discussion, in accordance with the teachings of the various references that are cited herein, and/or otherwise as will be apparent to those of ordinary skill in the art in view of the teachings herein.

A. Overview of Exemplary Ultrasonic Instrument with Translating Blade Sheath and Enhanced Gripping Features FIGS. 5-11B illustrate an exemplary ultrasonic surgical instrument (110) including an exemplary alternative end effector (140) that includes features to aid in blunt dissection; and an exemplary alternative gripping assembly (170) that includes adjustable features that aid an operator in grasping instrument (110). End effector (140) and gripping assembly (170) are discussed in further detail below. Although end effector (140) and/or handle assembly (120) may be readily incorporated into instrument (10) or other suitable instruments, each of these features are described herein with respect to instrument (110). Instrument (110) is substantially similar to instrument (10), except for the differences described below. Aside from the features described below, at least part of instrument (110) may be constructed and operable in accordance with any of the references that are cited herein.

Instrument (110) of the present example comprises a shaft assembly (130) that extends between end effector (140) and gripping assembly (170). Gripping assembly (170) includes a handle assembly (120) and clamp arm assembly (150) that an operator may grasp and manipulate in order to operate instrument (110), as discussed in further detail below. Handle assembly (120) comprises a body (122) including a finger grip (124) and a button (126). Clamp arm assembly (150) that is pivotable toward and away from body (122). A proximal portion of clamp arm assembly (150) comprises a thumb grip (152). Thumb grip (152) and finger grip (124) together provide a scissor grip type of configuration. It should be understood, however, that various other suitable configurations may be used, including but not limited to a pistol grip configuration. Moreover, many suitable grasping configurations by an operator are possible. For example, thumb grip (152) and finger grip (124) each may accommodate any of the thumb and/or fingers of an operator.

Figure 5:
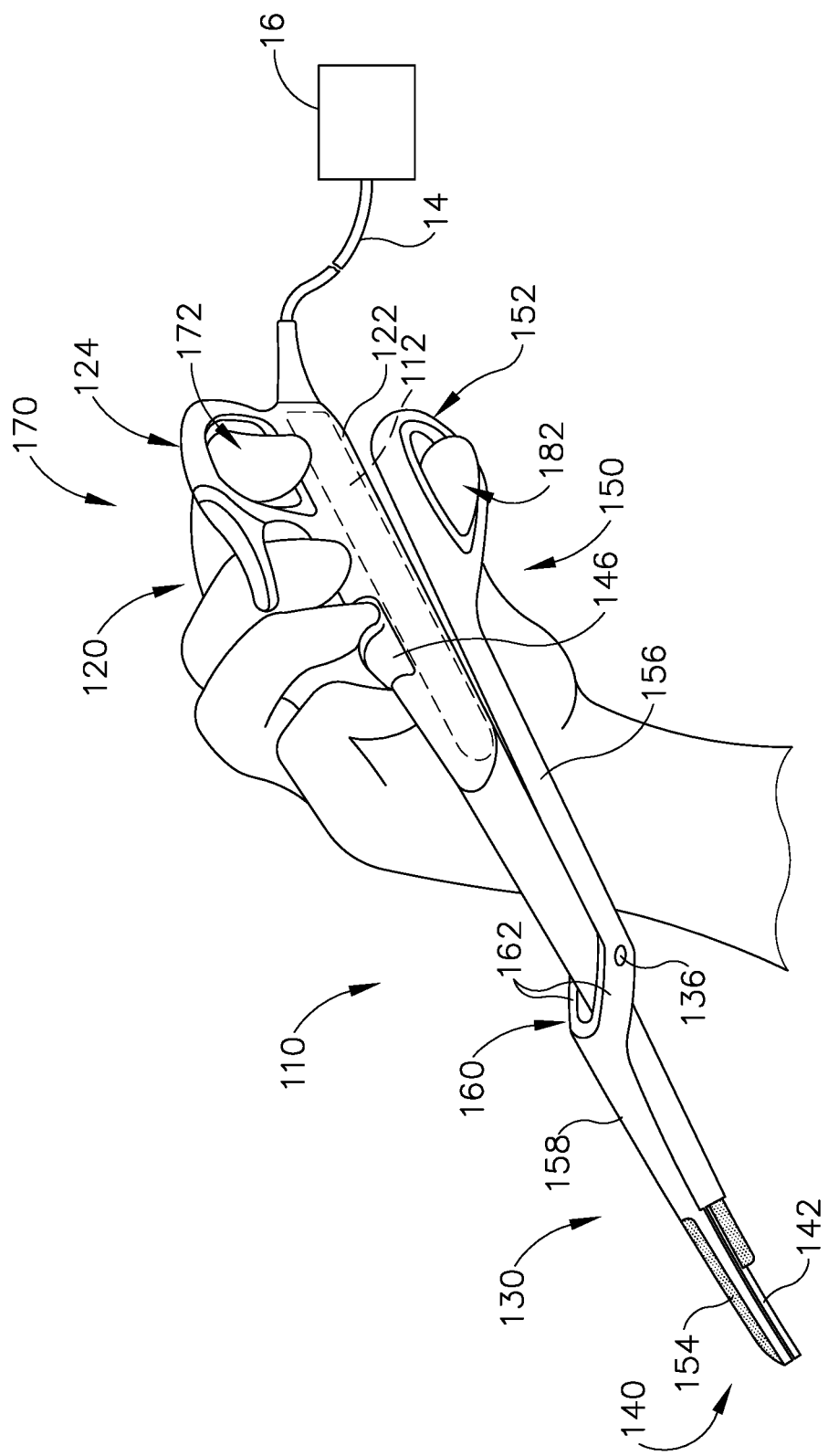
FIG. 5 depicts a perspective view of an exemplary alternative ultrasonic surgical instrument.
Figure 6:
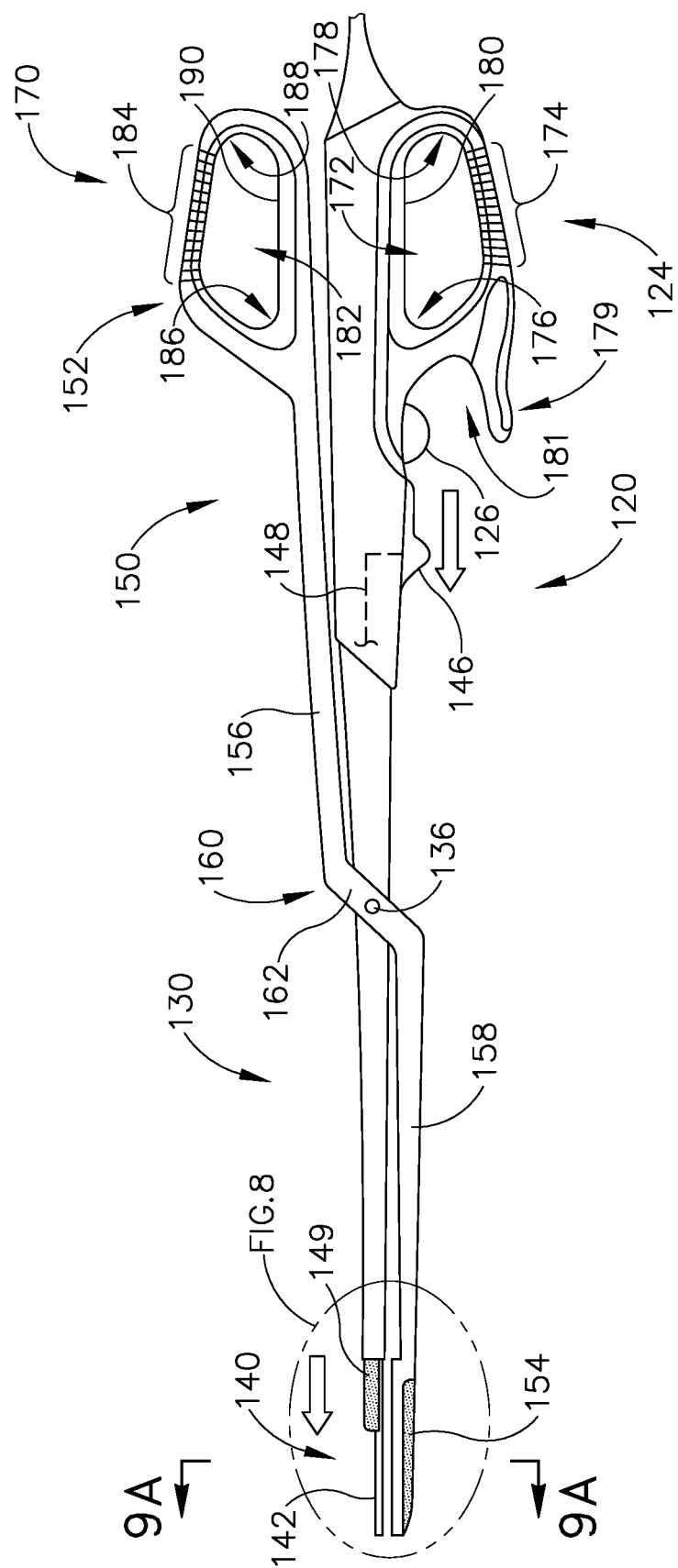
FIG. 6 depicts a side elevational view of the instrument of FIG. 5, with a slidable sheath of the instrument in a retracted position.

End effector (140) includes an ultrasonic blade (142) extending distally from shaft assembly (130); and a pivoting clamp arm (154), which is an integral feature of clamp arm assembly (150). Clamp arm assembly (150) is pivotably coupled to shaft assembly (130) via a pivot member (136) (e.g., a pin, bearing, shaft, etc.) such that clamp arm (154) is pivotable toward and away from ultrasonic blade (142) to thereby clamp tissue between a clamp pad (155) of clamp arm (154) and ultrasonic blade (142). As best seen in FIG. 5, clamp arm assembly includes a proximal portion (156), a distal portion (158), and a middle portion (160). As shown, middle portion (160) comprises a bifurcation defining first and second arms (162). Clamp arm assembly (150) is pivotably coupled to shaft assembly (130) due to first and second arms (162) being pivotally coupled about pivot member (136). Various other suitable ways in which clamp arm assembly (150) may be pivotally coupled to shaft assembly (130) will be apparent to persons skilled in the art in view of the teachings herein.

Clamp arm assembly (150) is configured such that clamp arm (154) is pivotable toward ultrasonic blade (142) in response to pivoting of thumb grip (152) of clamp arm assembly (150) toward body (122); and such that clamp arm (154) is pivotable away from ultrasonic blade (142) in response to pivoting of thumb grip (152) of clamp arm assembly (150) away from body (122). In some versions, one or more resilient members are used to bias clamp arm (154) to an open position. By way of example only, such a resilient member may comprise a leaf spring, a torsion spring, and/or any other suitable kind of resilient member.

As shown in FIG. 5, an ultrasonic transducer assembly (112) is positioned within body (122) of handle assembly (120). Transducer assembly (112) may be configured to operate substantially similar to transducer assembly (12). Other suitable forms and configurations that transducer assembly (112) may assume will be apparent to persons skilled in the art in view of the teachings herein. As shown, transducer assembly (112) is coupled with a generator (16) via a cable (14). While an acoustic waveguide is not shown in FIGS. 5-11B, it will be understood that an acoustic waveguide of instrument (110) extends through shaft assembly (130) and is configured substantially in accordance with waveguide (80) described above. Accordingly, when transducer assembly (112) is energized, ultrasonic mechanical oscillations of the waveguide are transmitted through the waveguide to reach ultrasonic blade (142), thereby providing oscillation of ultrasonic blade (142) at the resonant ultrasonic frequency. Thus, when tissue is secured between ultrasonic blade (142) and clamp arm (154), the ultrasonic oscillation of ultrasonic blade (142) may simultaneously sever the tissue and denature the proteins in adjacent tissue cells, thereby providing a coagulative effect with relatively little thermal spread. In some versions, end effector (140) is also operable to apply RF electrosurgical energy to tissue (e.g., in accordance with the teachings of references cited herein).

An operator may activate button (126) to thereby selectively activating transducer assembly (112) to activate ultrasonic blade (142). It will be understood that instrument (110) includes components similar to those described with respect to instrument (10) that cause the activation of transducer assembly (112) upon activation of button (126). In the present example, one button (126) is provided; however, in other examples, there may be multiple buttons (126), such as one for activating ultrasonic blade (142) at a low power level and another for activating ultrasonic blade (142) at a high power level. It should be understood that any other suitable number of buttons and/or otherwise selectable power levels may be provided. For instance, a foot pedal may be provided to selectively activate transducer assembly (112). Button (126) of the present example positioned such that an operator may readily fully operate instrument (110) with a single hand. For instance, the operator may position their thumb in the ring formed by thumb grip (152), position their middle or ring finger in the ring formed by finger grip (124), and manipulate button (126) using their index finger. Of course, any other suitable techniques may be used to grip and operate instrument (110); and button (26) may be located at any other suitable positions. In alternative examples, instrument (110) may include controls similar to other instruments described herein, in order to activate transducer assembly (112).

B. Exemplary Translating Blade Sheath

As noted above, end effector (140) includes features that aid in blunt dissection of tissue. As shown in FIGS. 6, 8, 9A-9B, 10B, and 11A-11B, end effector (140) includes a sheath (144) that is axially movable between a retracted position (FIGS. 6, 9A, and 10B) and an extended position (FIGS. 8, 9B, and 11A-11B). As shown in the present example, sheath (144) partially angularly envelops ultrasonic blade (142) such that tissue may be clamped between blade (142) and clamp arm (154) and subjected to mechanical oscillations of blade (142), without being impeded by sheath (144). In other words, blade (142) does not contact sheath (144). It should therefore be understood that end effector (140) may still be used to ultrasonically seal and sever tissue regardless of the position of sheath (144). However, in other examples, sheath (144) may fully envelop blade (142) such that when sheath (144) is in the extended position, end effector (140) may not be used to sever tissue using mechanical oscillations of blade (144).

Figure 8:
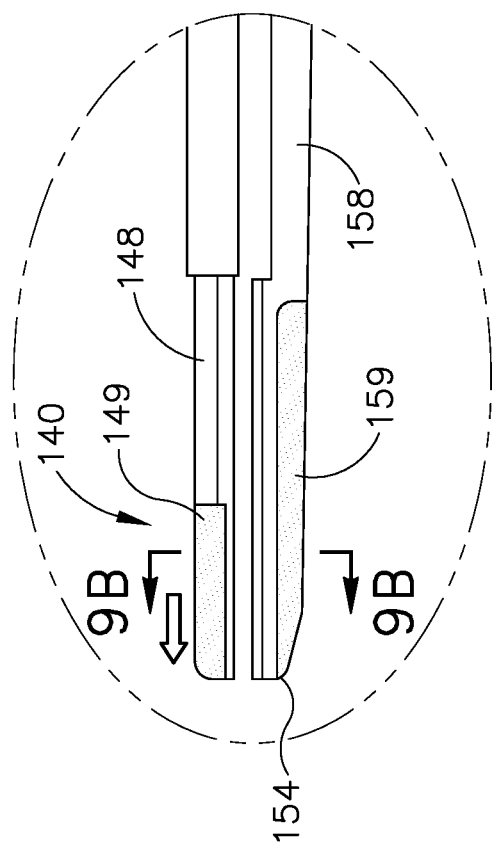
FIG. 8 depicts a detailed side elevational view of an end effector of the instrument of FIG. 5, showing the slidable sheath in an extended position.
Figure 10A:
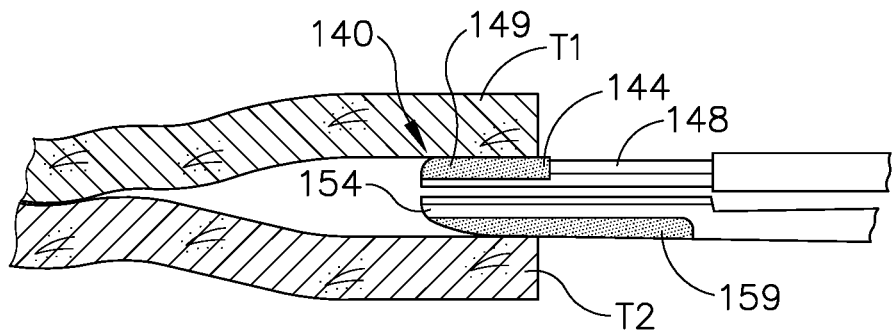
FIG. 10A depicts a side elevational view of a distal end of the end effector of FIG. 8, positioned between layers of tissue, showing the sheath in an extended position and the end effector in a closed position.
Figure 10B:
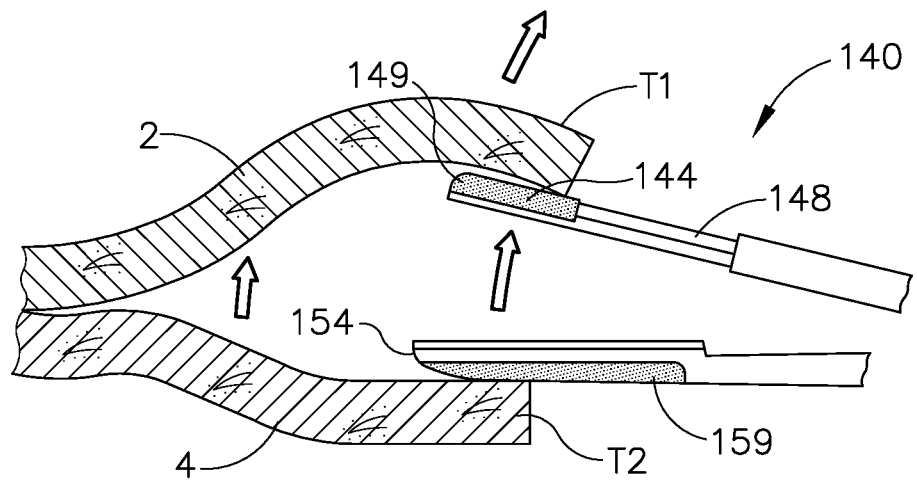
FIG. 10B depicts a side elevational view of a distal end of the end effector of FIG. 8, positioned between layers of tissue, showing the sheath in the extended position and the end effector in an open position to separate the layers of tissue.
Figure 11A:
FIG. 11A depicts a top plan view of tissue forming an anatomical passageway.
Figure 11B:
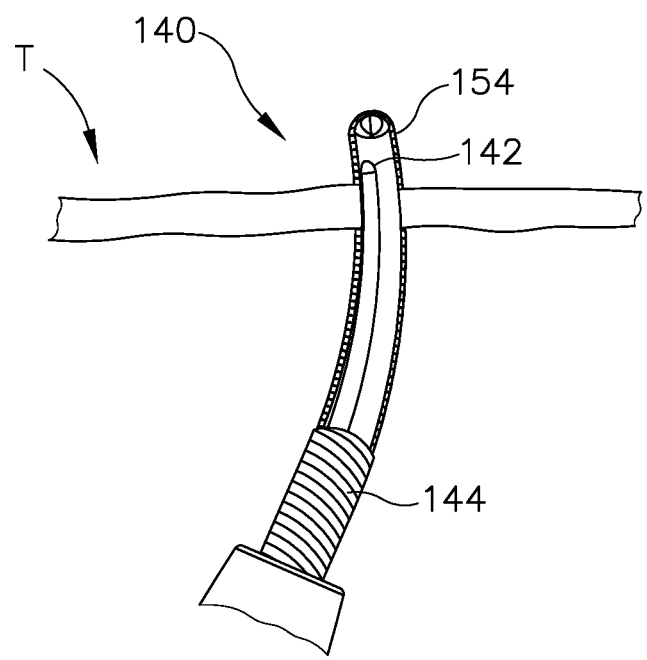
FIG. 11B depicts a top plan view of the end effector of FIG. 8, with the sliding sheath in a retracted position, being used to transect the anatomical passageway of FIG. 11A.

As shown, sheath (144) in the extended position increases the effective cross-sectional area of distal end of end effector (140) (e.g., taken along line 9B-9B of FIG. 8). Because the effective cross-sectional area of end effector (140) is increased, an operator may be less likely to pierce tissue during blunt dissection of tissue using end effector (140). In the present example, sheath (144) and clamp arm (154) include a textured surface to further aid in blunt dissection of tissue. Particularly, as best seen in FIGS. 8 and 11A-11B, sheath (144) and underside (156) of clamp arm (154) (i.e., the portion opposing clamp pad (155)) each include a knurled surface (149, 159), respectively. Knurled surfaces (148, 159) may enhance a grip between sheath (144) and tissue, and between clamp arm (154) and tissue, when end effector (140) is used to perform blunt dissection as shown in FIGS. 10A-10B and as will be described in greater detail below.

In the present example, knurled surfaces (149, 159) are machined onto sheath (144) and clamp arm (154). However, in other examples, knurled surfaces (149, 159) may be added to sheath (144) and clamp arm (154) in other suitable manners that will be apparent to persons skilled in the art in view of teachings herein. Moreover, rather than knurling, sheath (144) and/or clamp arm (154) may include other types of suitable textured surfaces, surface treatments, coatings, etc., that will be apparent to persons skilled in the art in view of the teachings herein.

In the present example, sheath (144) is operably connected to a slidable switch (146) via a mechanical link (148). As shown, moving switch (146) in the proximal direction moves link (148) and sheath (144) proximally, while moving switch (146) in the distal direction moves link (148) and sheath (144) distally. In other examples, sheath (144) may be axially movable by switch (146) in other suitable manners. In some variations, sheath (144) may move proximally in response to distal movement of switch (146), and distally in response to proximal movement of switch (146). In some other variations, switch (146) may comprise a push button or other mechanism, the depression of which mechanically or electronically causes movement of sheath (144). Other suitable manners of advancing and retracting sheath (144) will be apparent to persons skilled in the art in view of the teachings herein.

C. Exemplary Alternative Gripping Assembly with Adjustability Features

Some instruments having scissor grip configurations like that of instrument (10) include finger and thumb grips that are rigid. Such instruments may not allow the operator to customize the size and shape of the eyelets according to the operator's hand size, comfort level, and other preferences. In instrument (110), gripping assembly (170) includes a handle assembly (120) having an adjustable finger grip (124), and clamp arm assembly (150) having an adjustable thumb grip (152). Finger grip (124) and thumb grip (152) are each adjustable in order to accommodate operator hand size differences and gripping preferences.

Figure 7:
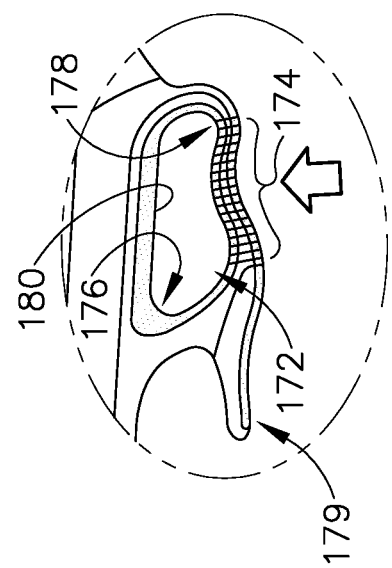
FIG. 7 depicts a detailed side elevational view of a portion of a gripping assembly of the instrument of FIG. 5.
Figure 9A:
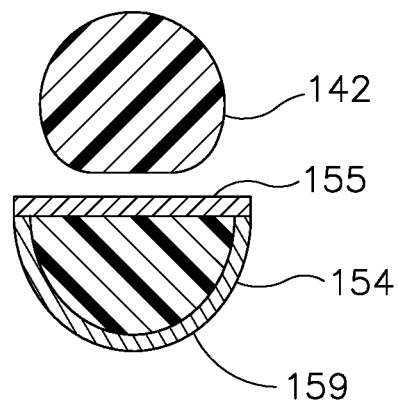
FIG. 9A depicts a cross-sectional view of the end effector of FIG. 8, taken along line 9A-9A of FIG. 6.
Figure 9B:
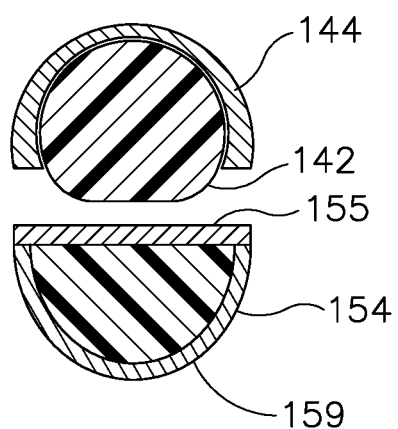
FIG. 9B depicts a cross-sectional view of the end effector of FIG. 8, taken along line 9B-9B of FIG. 8.

In particular, finger grip (124) defines an eyelet (172) having an adjustable member (174) that is movable relative to other portions of eyelet (172). As shown in FIG. 7, a portion of adjustable portion (174) may be directed inwardly toward the longitudinal axis of instrument (110) to effectively decrease the cross-sectional area of eyelet (172). Alternatively, a portion of adjustable member (174) may be directed outwardly away from the longitudinal axis of instrument (110) to effectively increase the cross-sectional area of eyelet (172). In some examples, some portions of adjustable member (174) may be moved toward the longitudinal axis while other portions of adjustable member (174) are simultaneously moved away from the longitudinal axis of instrument (110). As shown, adjustable member (174) encompasses only a certain portion of thumb grip (124) and eyelet (172). In other words, thumb grip (124) and eyelet (172) are adjustable as described above along only a portion of the perimeters thereof. However, adjustable member (174) may extend along a greater or lesser portion of such perimeters than the amount shown. Moreover, adjustable member (174) is shown to be a single continuous portion in the present example. However, in other examples, there may multiple adjustable members (174).

Finger grip (124) includes additional features that aid in the user gripping the gripping assembly (170). As shown, distal portion of eyelet (172) includes a first tapered section (176) and proximal portion of eyelet (172) includes a second tapered section (178). Inner surface (180) of eyelet (172) in the present example includes a surface with sufficient pliability to provide comfort to the operator but not so much pliability that could reduce the operator's control and responsiveness of instrument (110). Moreover, in the present example, inner surface (180) of eyelet (172) provides a coefficient of friction that is sufficient to assist in maintaining the position of operator's finger or thumb within eyelet (172) when movement of such is not desired, but also that allows the operator to move his or her finger or thumb within eyelet (172) when desired. As shown, clamp arm assembly (150) further includes a projection (179) extending distally from finger grip (152) that defines a space (181) for another finger of the operator. Thus, eyelet (172) is configured for an operator to suitably position a thumb or finger according to the operator's anatomical considerations and comfort preferences, among other things.

Similarly, thumb grip (152) defines an eyelet (182) having an adjustable member (184) that is movable relative to other portions of eyelet (182). Similar to adjustable portion (174) shown in FIG. 7, a portion of adjustable member (184) may be directed inwardly toward the longitudinal axis of instrument (110) to effectively decrease the cross-sectional area of eyelet (182). Alternatively, a portion of adjustable member (184) may be directed outwardly away from the longitudinal axis of instrument (110) to effectively increase the cross-sectional area of eyelet (182). In some examples, some portions of adjustable member (184) may be moved toward the longitudinal axis while other portions of adjustable member (184) are simultaneously moved away from the longitudinal axis of instrument (110). As shown, adjustable member (184) encompasses only a certain portion of thumb grip (124) and eyelet (182). In other words, thumb grip (124) and eyelet (182) are adjustable as described above along only a portion of the perimeters thereof. However, adjustable member (184) may extend along a greater or lesser portion of such perimeters than the amount shown. Moreover, adjustable member (184) is shown to be a single continuous portion in the present example. However, in other examples, there may multiple adjustable members (184).

Finger grip includes additional features that aid in the user gripping the gripping assembly (170). As shown, distal portion of eyelet (182) includes a first tapered section (186) and proximal portion of eyelet (182) includes a second tapered section (188). Inner surface (190) of eyelet (192) in the present example includes a surface with sufficient pliability to provide comfort to the operator but not so much pliability that could reduce the operator's control and responsiveness of instrument (110). Moreover, in the present example, inner surface (190) of eyelet (182) provides a coefficient of friction that is sufficient to assist in maintaining the position of operator's finger or thumb within eyelet (182) when movement of such is not desired, but also that allows the operator to move his or her finger or thumb within eyelet (182) when desired. Thus, eyelet (182) is configured for an operator to suitably position a thumb or finger according to the operator's anatomical considerations and comfort preferences, among other things.

In the present example, each adjustable member (174, 184) is deformable. By way of example only, adjustable member (184) may be malleably deformable. For instance, adjustable members (174, 184) may be configured to maintain their adjusted positions absent a sufficient adjustment force. Adjustment members (174, 184) may thus be configured to provide an amount of resistance that maintains the positions of adjustment members (174, 184) during use and manipulation of instrument (110). However, upon being subjected to such a sufficient adjustment force, adjustment members (174, 184) are configured to move in the direction of such force. In some other versions, adjustable members (174, 184) are resiliently deformable, plastically deformable, or otherwise deformable.

Adjustable members (174, 184) may comprise an internal deformable member, such as a metal wire, embedded within a flexible outer material. In other examples, adjustable members (174, 184) may comprise a plurality of interlocking members that are configured to provide deformability. For example, adjustable members (174, 184) may comprise one or more ratchet joints that may pivot and lock in certain positions. In some other examples, adjustable members (174, 184) may include pivotally connected members that are configured lock in particular rotational positions relative to one another (e.g., similar to a gooseneck configuration). Other suitable configurations and manners of imparting deformability to adjustable members (174, 184) will be apparent to persons skilled in the art in view of the teachings herein.

D. Exemplary Operation

Figure 11C:
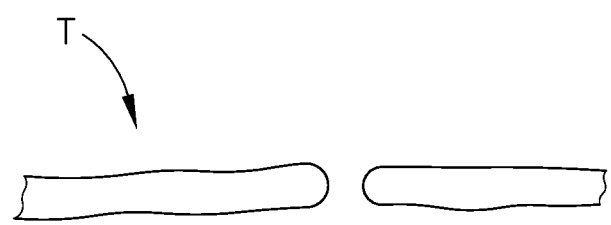
FIG. 11C depicts a top plan view of the anatomical passageway of FIG. 11A after being transected by the end effector of FIG. 8.

In an exemplary use for blunt dissection of tissue, sheath (144) may be advanced to the extended position as described above. End effector (140) may then be positioned between apposed layers of tissue (T1, T2) as shown in FIG. 10A. Due to the increased effective cross-sectional area of distal end of end effector (140) with sheath (144) in the extended position, the likelihood of blade (142) piercing tissue (T1, T2) may be reduced. To bluntly dissect or separate tissue layers (T1, T2), clamp arm (154) is pivoted away from ultrasonic blade (142) and sheath (144), as shown in FIG. 10B. Referring now to FIGS. 11A-11C, in some instances, instrument (110) is then used to transect tissue (T). Ultrasonic blade (142) and clamp arm (154) may be positioned around two layers of tissue. Clamp arm (154) is then closed relative to blade (142) to capture the layers of tissue between blade (142) and clamp pad (155) of clamp arm (154). Ultrasonic blade (142) may then be ultrasonically activated, such as in the manner discussed above, so that end effector (140) cuts and seals tissue (T). While sheath (144) is shown to be in a retracted position in FIG. 11B, in other examples, sheath (144) may be in the extended position (e.g., FIGS. 8, 9B, and 11A-11B) when blade (142) is activated. Blade (142) is activated for a sufficient amount of time such that tissue (T) is transected or severed, as shown in FIG. 11C.

In some instances, instrument (110) is used only to perform blunt dissection of tissue (T1, T2). In some other instances, instrument (110) is used only to sever tissue (T). In still other instances, instrument (110) is used to perform blunt dissection of tissue (T1, T2) before and/or after severing tissue (T), in the same surgical procedure. It should be understood that the diverse functionalities of instrument (110) may reduce the total number of different kinds of instruments that are needed to perform a surgical procedure.

III. Exemplary Alternative Ultrasonic Surgical Instrument with Touch Activation Sensor In addition to (or as an alternative to) providing enhanced ergonomics through the configuration of grips (124, 152) as described above, variations of instrument (10, 110) may provide enhanced ergonomics by providing alternatives to buttons (26, 126). In particular, it may be desirable to provide one or more features that are operable to ultrasonically activate blade (42, 142) and that are readily accessible by the operator's hand regardless of whether the operator chooses to grasp instrument (10, 110) using one particular gripping configuration or another particular gripping configuration. In other words, it may be desirable to enable the operator to easily activate blade (42, 142) regardless of how the operator chooses to grasp instrument (10, 110). The below discussion provides several examples of variations that may be used to provide alternatives to buttons (26, 126). Still other examples will be apparent to those of ordinary skill in the art in view of the teachings herein.

A. Ultrasonic Surgical Instrument with Activation Area on Handle Assembly

Figure 12:
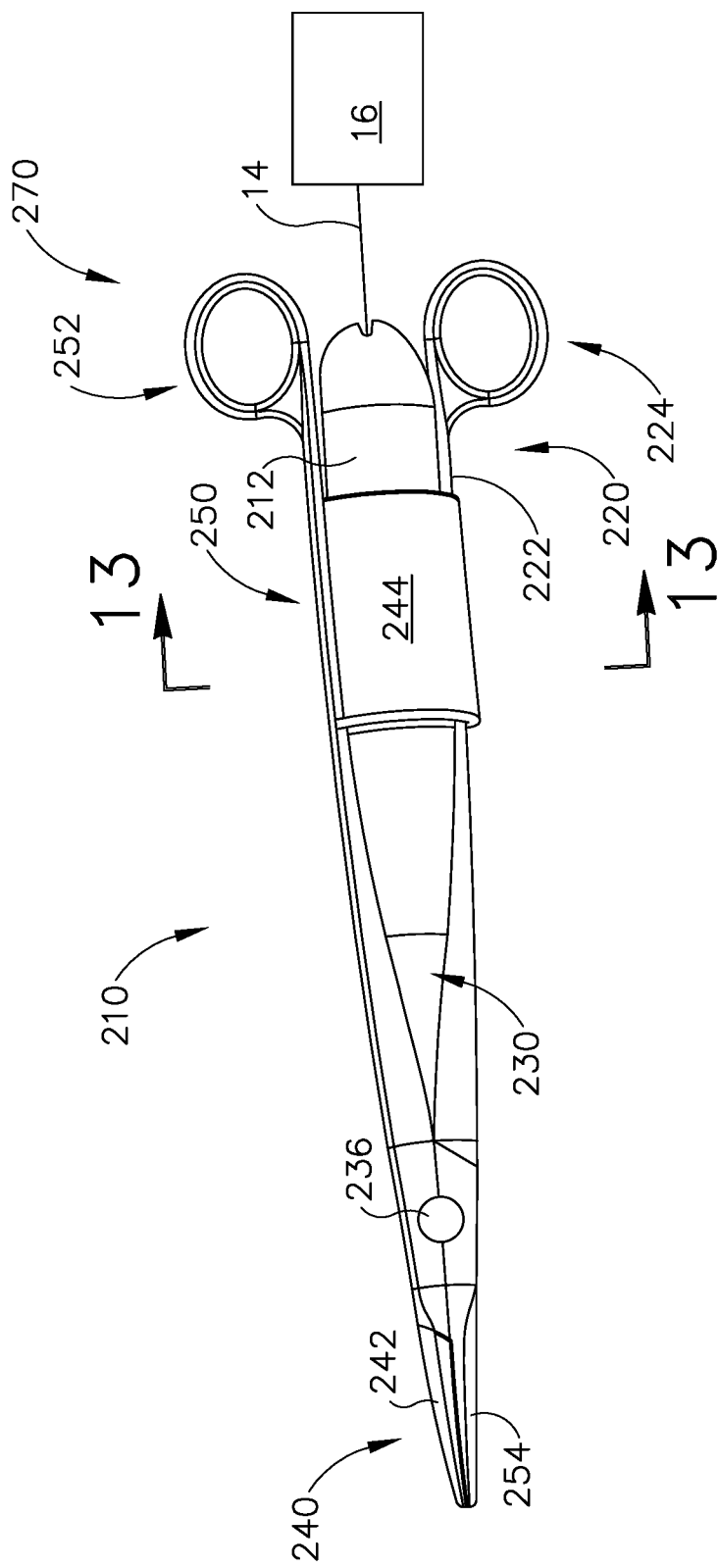
FIG. 12 depicts a perspective view of another exemplary alternative ultrasonic surgical instrument.

FIG. 12 shows another exemplary alternative ultrasonic surgical instrument (210). Instrument (210) is similar to instrument (10, 110), except for the differences discussed below. In the present example, instrument (210) is configured to be activated by a user activating an activation area (244), as discussed in further detail below, rather than by button(s) (26, 126). While activation area (244) is shown and described in the context of instrument (210), it should be understood that activation area (244) and variations thereof may be readily incorporated into instruments (10, 210) above, for example, to activate transducer (12, 112). Aside from the features described below, at least part of instrument (210) may be constructed and operable in accordance with any of the references that are cited herein.

Instrument (210) of the present example comprises a shaft assembly (230) and an end effector (240) that are operably coupled to a gripping assembly (270). Gripping assembly (270) includes a handle assembly (220) and clamp arm assembly (250) that an operator may grasp and manipulate in order to operate instrument (210), as discussed in further detail below. Handle assembly (220) comprises a body (222) including a finger grip (224). Clamp arm assembly (250) is pivotable toward and away from body (222). A proximal portion of clamp arm assembly (250) comprises a thumb grip (252). Thumb grip (252) and finger grip (224) together provide a scissor grip type of configuration. It should be understood, however, that various other suitable configurations may be used, including but not limited to a pistol grip configuration. Moreover, many suitable grasping configurations by an operator are possible. For example, thumb grip (252) and finger grip (242) each may accommodate any of the thumb and/or fingers of an operator.

End effector (240) includes an ultrasonic blade (242) extending distally from shaft assembly (230); and a pivoting clamp arm (254), which is an integral feature of clamp arm assembly (250). Clamp arm assembly (250) is pivotably coupled to shaft assembly (230) via a pivot member (236) (e.g., a pin, bearing, shaft, etc.) such that clamp arm (254) is pivotable toward and away from ultrasonic blade (242) to thereby clamp tissue between a clamp pad (e.g., like clamp pad (155)) of clamp arm (154) and ultrasonic blade (242). Various other suitable ways in which clamp arm assembly (250) may be pivotally coupled to shaft assembly (230) will be apparent to persons skilled in the art in view of the teachings herein.

Clamp arm assembly (250) is configured such that clamp arm (254) is pivotable toward ultrasonic blade (242) in response to pivoting of thumb grip (252) of clamp arm assembly (250) toward body (222); and such that clamp arm (254) is pivotable away from ultrasonic blade (242) in response to pivoting of thumb grip (252) of clamp arm assembly (250) away from body (222). In some versions, one or more resilient members are used to bias clamp arm (254) to an open position. By way of example only, such a resilient member may comprise a leaf spring, a torsion spring, and/or any other suitable kind of resilient member.

Figure 13:
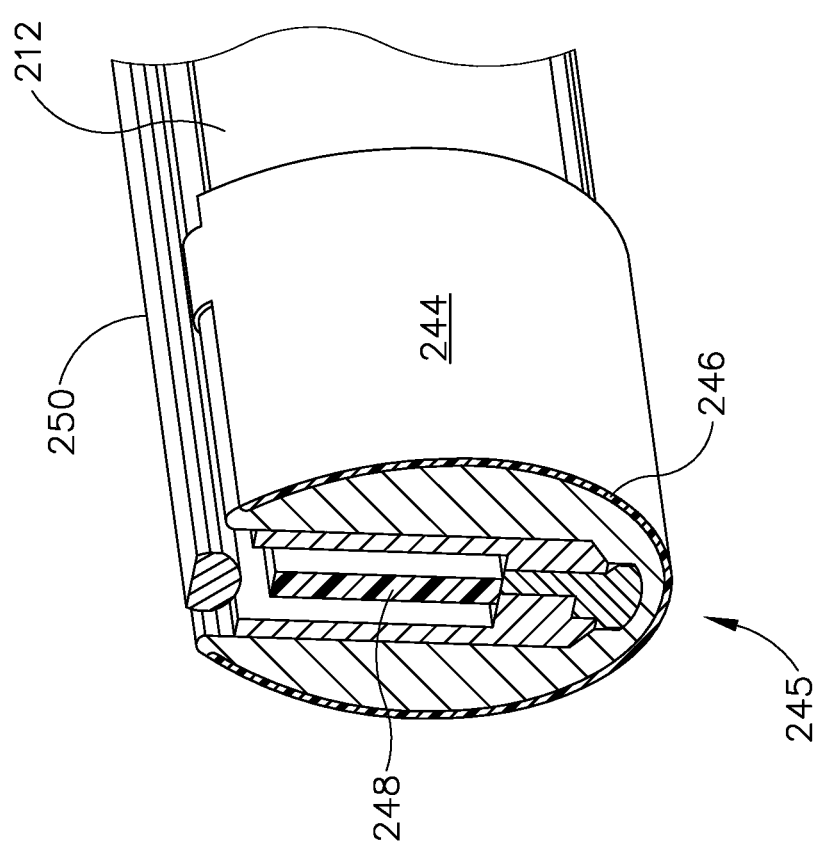
FIG. 13 depicts a cross-sectional view of the instrument of FIG. 12, taken along line 13-13 of FIG. 12.

An ultrasonic transducer assembly (212) is positioned within body (222) of handle assembly (220). Transducer assembly (212) may be configured to operate substantially similar to transducer assembly (12, 112). Other suitable forms and configurations that transducer assembly may assume will be apparent to persons skilled in the art in view of the teachings herein. As shown, transducer assembly (212) is coupled with a generator (16) via a cable (14). While an acoustic waveguide is not shown in FIGS. 12-13, it will be understood that an acoustic waveguide of instrument (210) extends through shaft assembly (230) and is configured substantially in accordance with waveguide (80) described above. Accordingly, when transducer assembly (212) is energized, ultrasonic mechanical oscillations of the waveguide are transmitted through the waveguide to reach ultrasonic blade (242), thereby providing oscillation of ultrasonic blade (242) at the resonant ultrasonic frequency. Thus, when tissue is secured between ultrasonic blade (242) and clamp arm (254), the ultrasonic oscillation of ultrasonic blade (242) may simultaneously sever the tissue and denature the proteins in adjacent tissue cells, thereby providing a coagulative effect with relatively little thermal spread. In some versions, end effector (240) is also operable to apply RF electrosurgical energy to tissue (e.g., in accordance with the teachings of references cited herein).

As noted above, handle assembly (220) of the present example further comprises an activation area (244), which is configured to activate transducer assembly (212) upon receiving a suitable input gesture (e.g., touch gesture) from an operator. Activation area (244) in the present example comprises a touch sensor (245) which, as seen best in FIG. 13, takes the form of film (246) extending from one side of handle assembly (220) to the other side of handle assembly (220). By way of example only, film (246) may comprise a capacitive touch sensitive film. Film (246) is in communication with printed circuit board (248), which includes components that are operable to convert touches/gestures sensed by sensor (245) into control signals that activate transducer (212). Thus, upon sensor (245) sensing a suitable touch gesture, circuit board (248) communicates such information to transducer (212) to thereby activate transducer (212). As shown in the present example, activation area (244) is shown to only be positioned a particular portion of handle assembly (220). However, in other examples, activation area (244) may cover a larger portion of the surface area of handle assembly (220). Additionally or alternatively, there may be additional activation areas (244) positioned on the handle assembly (220) or on other components of instrument (210). For example, activation area(s) (244) may encompass substantially all of the surface area of instrument (210) such that an operator can essentially provide an input gesture to any portion of instrument (210) in order to activate transducer assembly (212).

In versions of instrument (210) where more than one sensor (245) is provided, the different sensors (245) may provide different responses. For instance, one sensor (245)

may provide ultrasonic activation of blade (242) at a first power level while another sensor (245) may provide ultrasonic activation of blade (242) at a second power level. In addition or in the alternative, one sensor (245) may provide RF electrosurgical activation of end effector (240) while another one or more sensors (245) may provide ultrasonic activation of blade (242). Regardless of the number of sensors (245), sensor (245) may provide different responses based on how the operator touches sensor (245). For instance, as will be described in greater detail below, sensor (245) may provide one response when an operator taps sensor (245), and a different response when the operator slides a finger along sensor (245), and/or another different response when the operator maintains contact with sensor (245).

Figure 14:
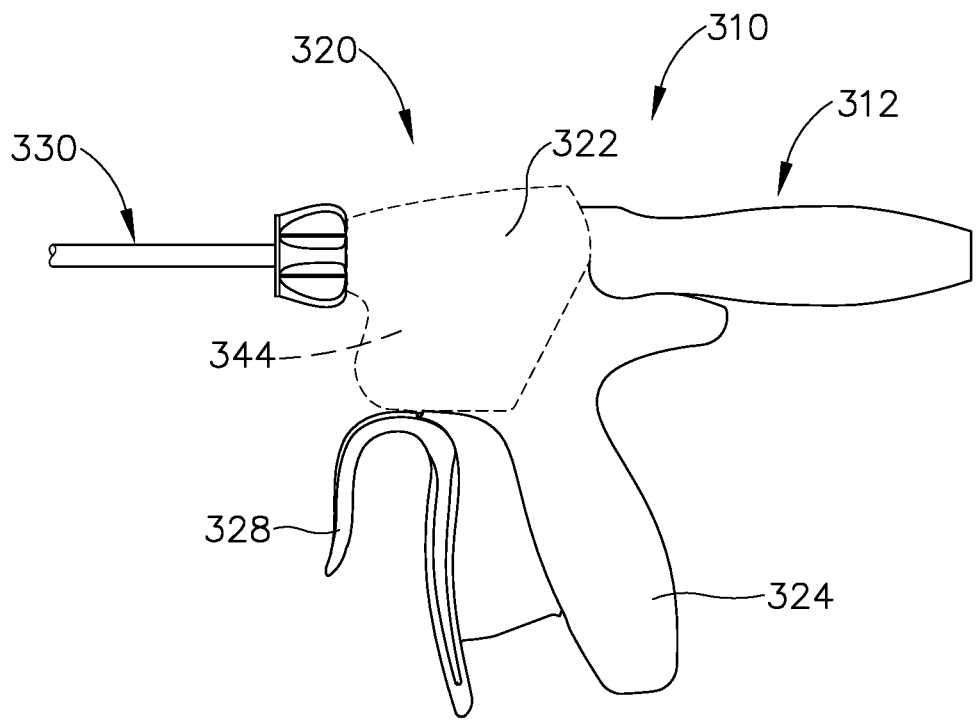
FIG. 14 depicts a side elevational view of an exemplary alternative handle assembly that is suitable for incorporation into an ultrasonic surgical instrument, showing one exemplary configuration of an activation area on the handle assembly.
Figure 15:
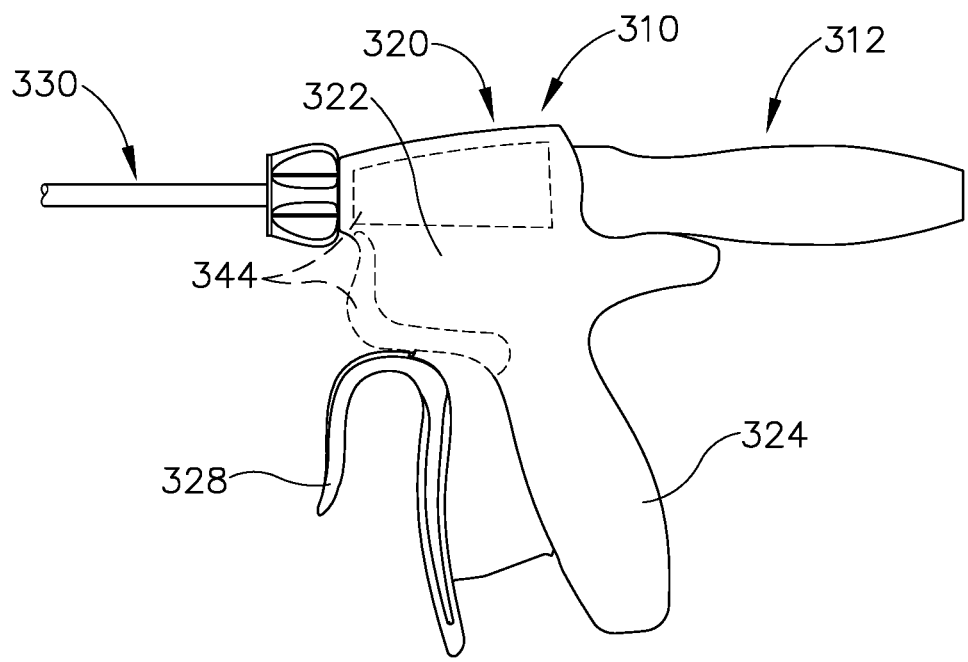
FIG. 15 depicts a side elevational view of another exemplary alternative handle assembly that is suitable for incorporation into an ultrasonic surgical instrument, showing another exemplary configuration of an activation area on the handle assembly.

FIGS. 14 and 15 show another exemplary alternative ultrasonic instrument (310) having a pistol grip configuration. As discussed below, similar to instrument (210), instrument (310) may be activated in response to a suitable input gesture on an activation area (344), rather than utilizing buttons (26, 126). At least part of instrument (310) may be constructed and operable in accordance with any of the references that are cited herein.

Instrument (310) of the present example comprises a handle assembly (320) and a shaft assembly (330). While an end effector is not shown, it will be understood that end effector includes an ultrasonic blade and a pivoting clamp arm, which may be configured and operable in accordance with the teachings of various references cited herein. Instrument (310) further includes a transducer assembly (312) that generates ultrasonic vibrations that are communicated to ultrasonic blade of instrument (310) in the same manner as described above with respect to transducer assembly (12, 112, 212) and ultrasonic blade (42, 142, 242). Moreover, it will be understood that transducer assembly (312) may be coupled to a generator via a cable.

Handle assembly (320) comprises a body (322) including a pistol grip (324) and a trigger (328) that is pivotable toward and away from pistol grip (324) to pivot the clamp arm relative to the ultrasonic blade. However, rather than including buttons, instrument (310) includes an activation area (344) which, upon receiving a suitable touch gesture from an operator, is configured to activate transducer assembly (312). By way of example only, activation area (344) may comprise one or more sensors such as a capacitive touch sensitive film. Other suitable components and features that may be used to form activation area (344) will be apparent to those of ordinary skill in the art in view of the teachings herein.

FIG. 14 shows one exemplary form that activation area (344) may take. In this example, activation area (344) encompasses a substantial portion of body (322) of handle assembly (320). Particularly, activation area (344) extends from a proximal portion of body (322), around distal portion of body, and substantially from trigger (328) to an upper portion of body (322). In this configuration, an operator may activate activation area (344) using a finger and/or thumb of the same hand that grasps pistol grip (324); or using the operator's other hand. FIG. 15 shows another exemplary form that activation area (344) may take. In this example, activation area (344) covers less surface area of body (322) than in the example of FIG. 14. In the example of FIG. 15, activation area (344) encompasses the distal portion of body (322), as well as upper and lower lateral portions of body (322). In still other examples, activation area (344) may encompass different or additional parts of handle assembly (320). For example, in some examples, activation area (344) may encompass the entire body (322) or entire handle assembly (320). Other suitable forms that activation area (344) may take will be apparent to persons skilled in the art in view of the teachings herein.

In the present example, an operator may activate transducer (212, 312) of instrument by performing any suitable touch gesture on activation area (244, 344), using one or more fingers of an operator. Alternative, rather than using the fingers of an operator, a sufficient input device (e.g., a stylus), may be utilized in addition or in the alternative to the operator's fingers. Such suitable touch gestures may include tapping, sliding/swiping, pressing and holding, any other suitable touch gestures that will be understood by persons skilled in the art in view of the teachings herein, as well as any variations and/or combinations of such touch gestures. Thus, in the example shown, activation area (244, 344) is configured to detect a touch gesture and activate transducer (212, 312) or otherwise activate end effector (240) based on such touch gesture.

In some examples, activation area (244, 344) is configured to detect different touch gestures, and to communicate such different inputs so that transducer assembly (212, 312) is activated in different activation modes. By way of example only, tapping activation area (244, 344) may toggle power levels (e.g., within the ultrasonic modality) or toggle modalities (e.g., RF versus ultrasonic) or simply trigger activation of blade (242)/end effector (240). By way of further example, sliding a finger along activation area (244, 344) may provide variable selection of a power level (e.g., within the ultrasonic modality). For instance, upon receiving one type of touch gesture (e.g., proximal swipe), transducer assembly (212, 312) may be activated in a first activation mode, (e.g., an activation mode associated with a "minimum" ultrasonic energy level that results in only the sealing of tissue). Similarly, upon receiving a second type of touch gesture (e.g., distal swipe), transducer assembly (212) may be activated in a second activation mode (e.g., an activation mode associated with a "maximum" ultrasonic energy level that results in the sealing and cutting of tissue). In the examples shown in FIGS. 12-15, activation area (244, 344) is configured to detect and resolve a single touch gesture, such as a tapping, sliding/swiping, or pressing and holding of a single finger. However, in other examples, activation area (244, 344) may be configured to detect and resolve other types of input touch gestures, including single touch with gesture (also known as "two-finger gestures," "dual touch," "dual control," and "gesture touch"), two touch, and multi-touch. Other suitable kinds of gestures that may be sensed by activation area (244, 344), and various different ways in which instrument (210, 310) may respond to such different gestures, will be apparent to those of ordinary skill in the art in view of the teachings herein. Moreover, it should be understood that instrument (210, 310) may be configured to allow the operator to program instrument (210, 310) such that the operator may select particular gestures that are available and corresponding responses to selected gestures.

It should also be understood that various kinds of touch sensitive features may be used to sense touching of activation areas (244, 344). By way of example only, activation areas (244, 344) may comprise projected capacitive touch sensors, bending wave sensors, infrared sensors, optical sensors, resistive sensors, surface acoustic wave sensors, surface capacitive sensors, or other suitable types of sensors. In examples utilizing multiple sensors (245), instrument (210) may utilize a single type of sensor, or multiple types of sensors. Other suitable forms and configurations that sensor (245) may take will be apparent to persons skilled in the art in view of the teachings herein.

B. Ultrasonic Surgical Instrument with Adaptable Activation Area

Figure 16A:
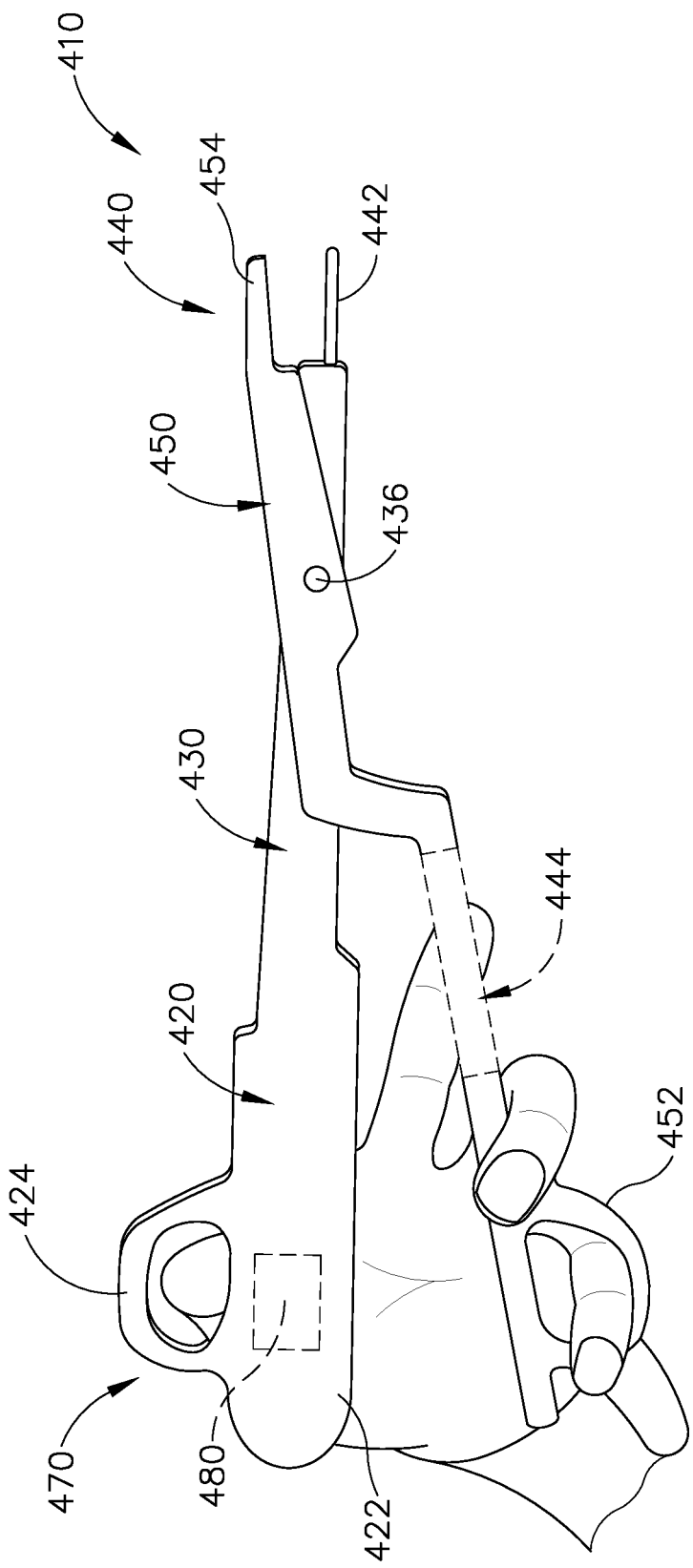
FIG. 16A depicts a side elevational view of another exemplary alternative ultrasonic instrument, showing the instrument being manipulated by an operator using a first exemplary grip configuration.
Figure 16B:
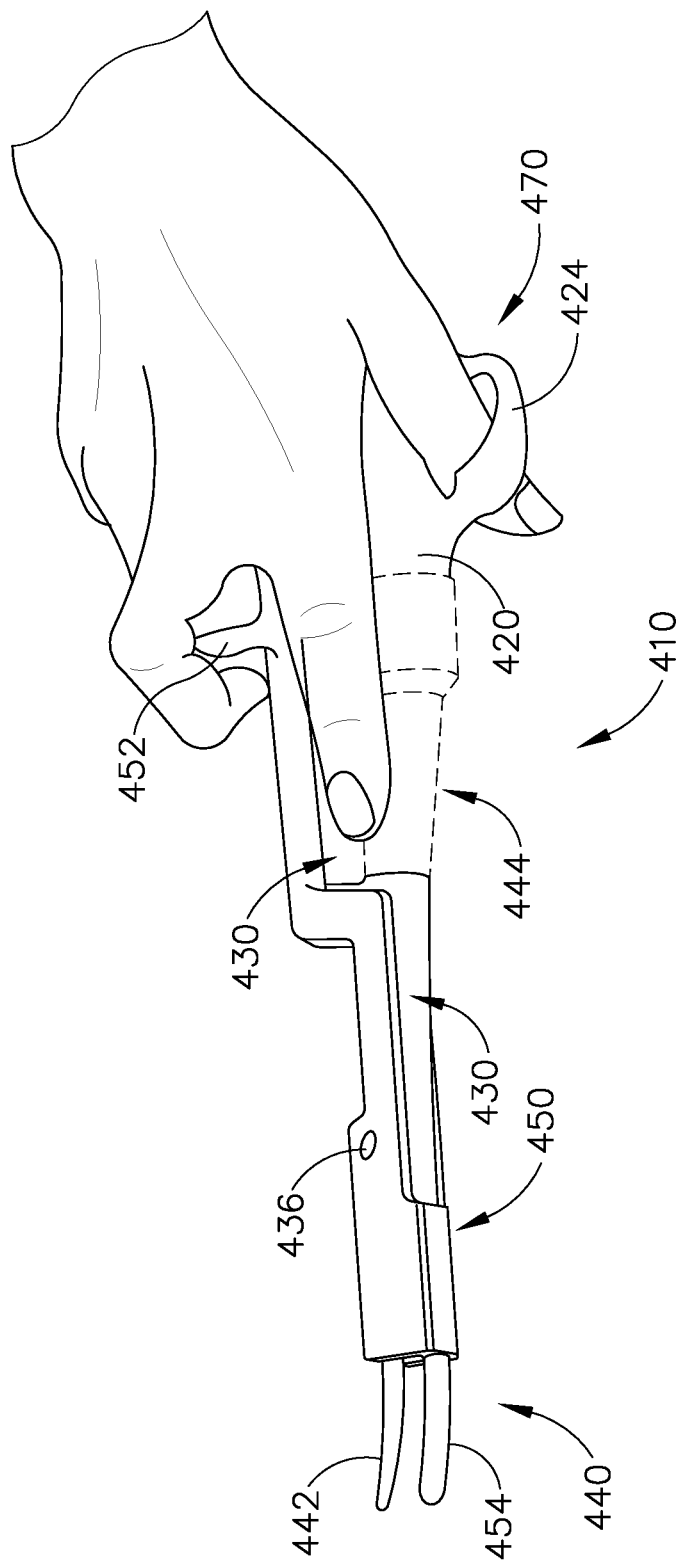
FIG. 16B depicts a perspective view of the instrument of FIG. 16A, showing the instrument being manipulated by an operator using a second exemplary grip configuration.
Figure 16C:
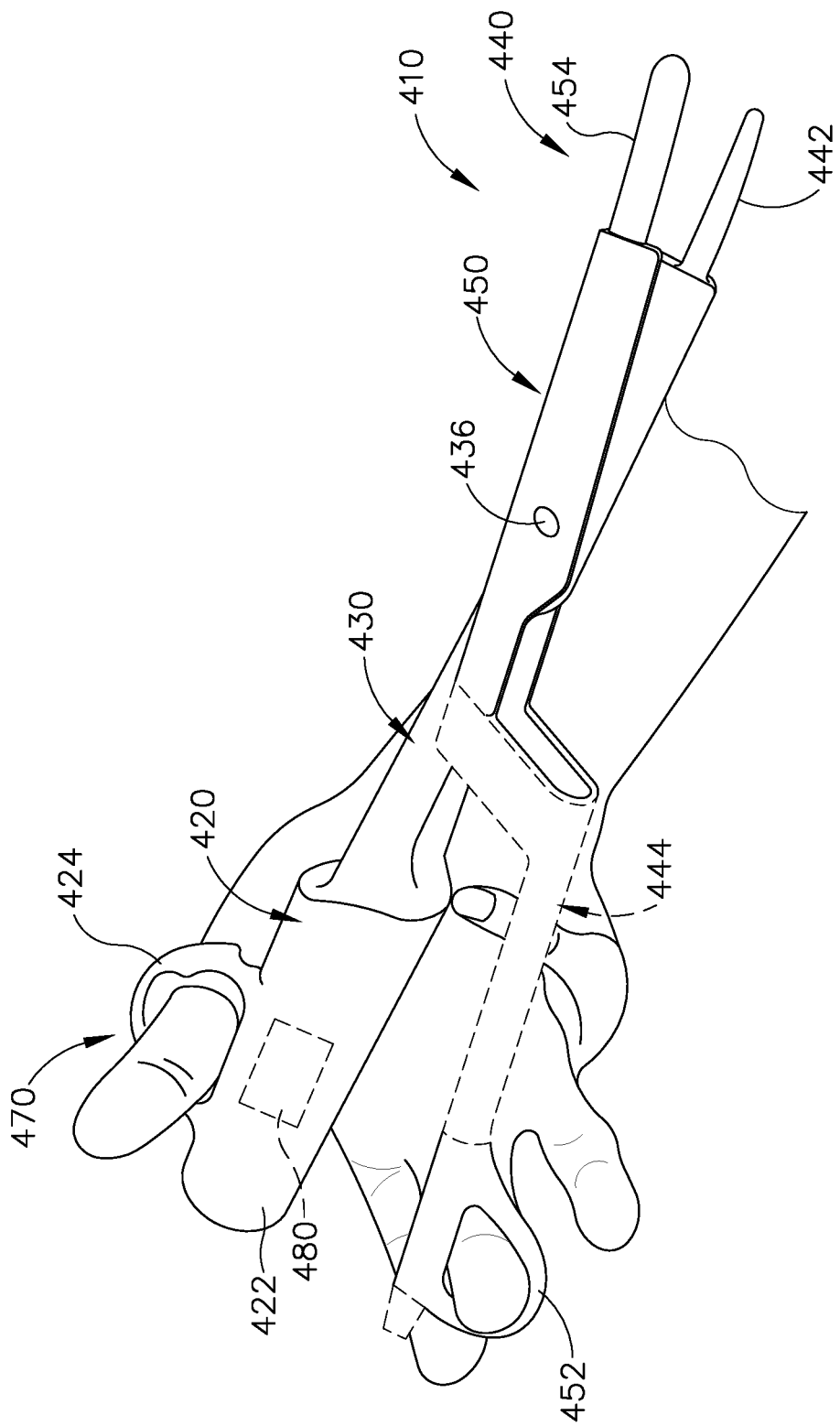
FIG. 16C depicts an alternative perspective view of the instrument of FIG. 16A, showing the instrument being manipulated by an operator using a third exemplary grip configuration.

FIGS. 16A-16C show another exemplary alternative surgical instrument (410).

Instrument (410) is similar to instrument (10, 110, 210), except for the differences discussed below. In the present example, instrument (410) is configured to be activated by a user activating an activation area (444), as discussed in further detail below, rather than by button(s) (26, 126). Aside from the features described below, at least part of instrument (410) may be constructed and operable in accordance with any of the references that are cited herein.

Instrument (410) of the present example comprises a shaft assembly (430) and an end effector (440) that are operably coupled to a gripping assembly (470). Gripping assembly (470) includes a handle assembly (420) and clamp arm assembly (450) that an operator may grasp and manipulate in order to operate instrument (410), as discussed in further detail below. Handle assembly (420) comprises a body (422) including a thumb grip (424). Clamp arm assembly (450) is pivotable toward and away from body (422). A proximal portion of clamp arm assembly (450) comprises a finger grip (452). Finger grip (452) and thumb grip (424) together provide a scissor grip type of configuration. It should be understood, however, that various other suitable configurations may be used, including but not limited to a pistol grip configuration. Moreover, many suitable grasping configurations by an operator are possible. For example, thumb grip (452) and finger grip (442) each may accommodate any of the thumb and/or fingers of an operator.

End effector (440) includes an ultrasonic blade (442) extending distally from shaft assembly (430); and a pivoting clamp arm (454), which is an integral feature of clamp arm assembly (450). Clamp arm assembly (450) is pivotably coupled to shaft assembly (430) via a pivot member (436) (e.g., a pin, bearing, shaft, etc.) such that clamp arm (454) is pivotable toward and away from ultrasonic blade (442) to thereby clamp tissue between a clamp pad (e.g., like clamp pad (155)) of clamp arm (154) and ultrasonic blade (442). Various other suitable ways in which clamp arm assembly (450) may be pivotally coupled to shaft assembly (430) will be apparent to persons skilled in the art in view of the teachings herein.

An ultrasonic transducer assembly (not shown) may be is positioned within body (422) of handle assembly (420). The transducer assembly may be configured to operate substantially similar to transducer assembly (12, 112, 212) described above. Accordingly, when the transducer assembly is energized, the resulting ultrasonic mechanical oscillations may be transmitted through an acoustic waveguide to reach ultrasonic blade (442), thereby providing oscillation of ultrasonic blade (442) at the resonant ultrasonic frequency. Thus, when tissue is secured between ultrasonic blade (442) and clamp arm (454), the ultrasonic oscillation of ultrasonic blade (442) may simultaneously sever the tissue and denature the proteins in adjacent tissue cells, thereby providing a coagulative effect with relatively little thermal spread. In some versions, end effector (440) is also operable to apply RF electrosurgical energy to tissue (e.g., in accordance with the teachings of references cited herein).

As noted above, instrument (410) of the present example further includes a plurality of activation areas (444), rather than including button(s) (e.g., buttons (26, 126), for activating the transducer assembly. Upon receiving a suitable touch gesture from an operator, an activation area (444) is configured to activate the transducer assembly in a manner that is substantially identical to that described above with respect to activation areas (244, 344). In versions where a plurality of activation areas (444) are substantially contiguous with each other, such activation areas (444) may be considered as a single activation area (444). For example, where instrument includes a series of substantially contiguous activation areas (444), instrument (410) may be considered to include a single activation area (444).

Different activation areas (444) or portions of activation areas (444) may be active depending on the orientation of instrument (410) and/or the position of the operator's hand relative to instrument (410). "Active," as described herein with respect to an activation area (444), is meant to refer to a state where inputting a sufficient input gesture to such activation area (444) results in the activation of transducer assembly (412). In other words, an active activation area (444) will be responsive to operator input, such that blade (442) will be activated in response to the operator touching the active activation area (444). When one activation area (444) of instrument (410) is active, the other activation areas (444) may be rendered inactive. An inactive activation area (444) may be non-responsive to operator input, such that blade (442) will not be activated in response to the operator touching the inactive activation area (444). It should be understood that an active activation area (444) may be configured and operable just like activation areas (244, 344) described above.

In the example shown, instrument (410) includes a sensor (480) that is configured to sense the position and/or orientation of instrument (410). As shown, sensor (480) is positioned on handle assembly (420) of instrument (410). However, in other examples, sensor (480) may be positioned on other portions of instrument (410). Moreover, in other examples, there may be more than one sensor (480). In the present example, sensor (480) comprises a gyroscopic sensor. However, in other examples, sensor (480) may comprise an accelerometer and/or any other suitable type of sensor. In some examples where instrument includes multiple sensors (480), instrument (410) may include a combination of different types of sensors (480), such as both gyroscopic sensors and accelerometers.

Figure 18:
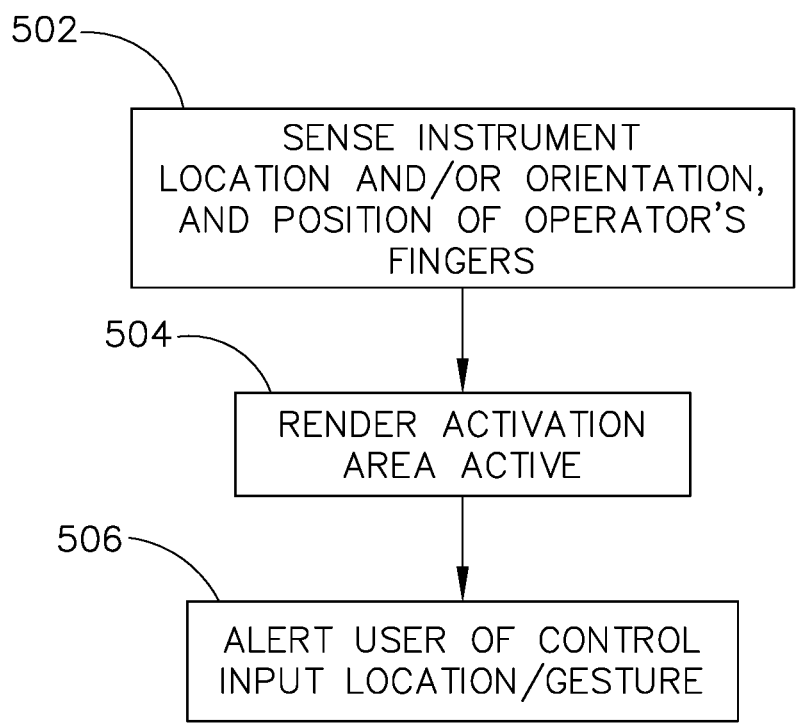
FIG. 18 depicts a flowchart showing steps of an exemplary method for programming a control scheme of a surgical instrument.

In the present example, referring also to FIG. 18, in response to sensing a particular position and/or orientation of instrument (410) (block 502), one of the plurality of activation areas (444) may be rendered active (block 504). For example, when sensor (480) senses that instrument (410) is in the position and orientation shown in FIG. 16A, an activation area (444) positioned on an intermediate region of clamp arm assembly (450) may be rendered active while other activation areas (444) are rendered inactive. Similarly, when sensor (480) senses that instrument (410) is in the position and orientation shown in FIG. 16B, an activation area (444) on body (422) of handle assembly (420) may be rendered active while other activation areas (444) are rendered inactive. Further, when sensor (480) senses that instrument (410) is in the position and orientation shown in FIG. 16C, an activation area (444) positioned on a proximal-most region and on an intermediate region of clamp arm assembly (450) may be rendered active while other activation areas (444) are rendered inactive. The activation areas (444) shown in FIGS. 16A-16C that are rendered active in response to the particular positions shown are merely exemplary. Thus, it will be understood that alternative or additional activation areas (444) may be rendered active in response to instrument (410) being oriented and grasped in such positions. Moreover, it will be understood that instrument (410) may be grasped and oriented in positions other than those shown, and that various activation areas (444) may be rendered active in response to instrument (410) being grasped and oriented in such positions.

In addition or in the alternative to sensing the position and/or orientation of instrument (410), instrument (410) may include sensors that are configured to sense the position of an operator's hand, fingers, or thumb relative to instrument (410). For example, as discussed above, activation areas (444) comprise one or more sensors, that upon receiving a suitable touch gesture from an operator, communicate a signal to activate the transducer assembly. These same sensors may also be utilized to sense the positioning of an operator's hand, fingers, or thumb. For example, sensors may sense the presence of the operator's finger, thumb, or other portion of the operator's hand, and may render one or more particular activation areas (444) active based at least in part on the sensed grip of the operator's hand on instrument (410). In other examples, however, a different sensor or set of sensors may be utilized for detecting the position of an operator's hand, fingers, or thumb.

Figure 17:
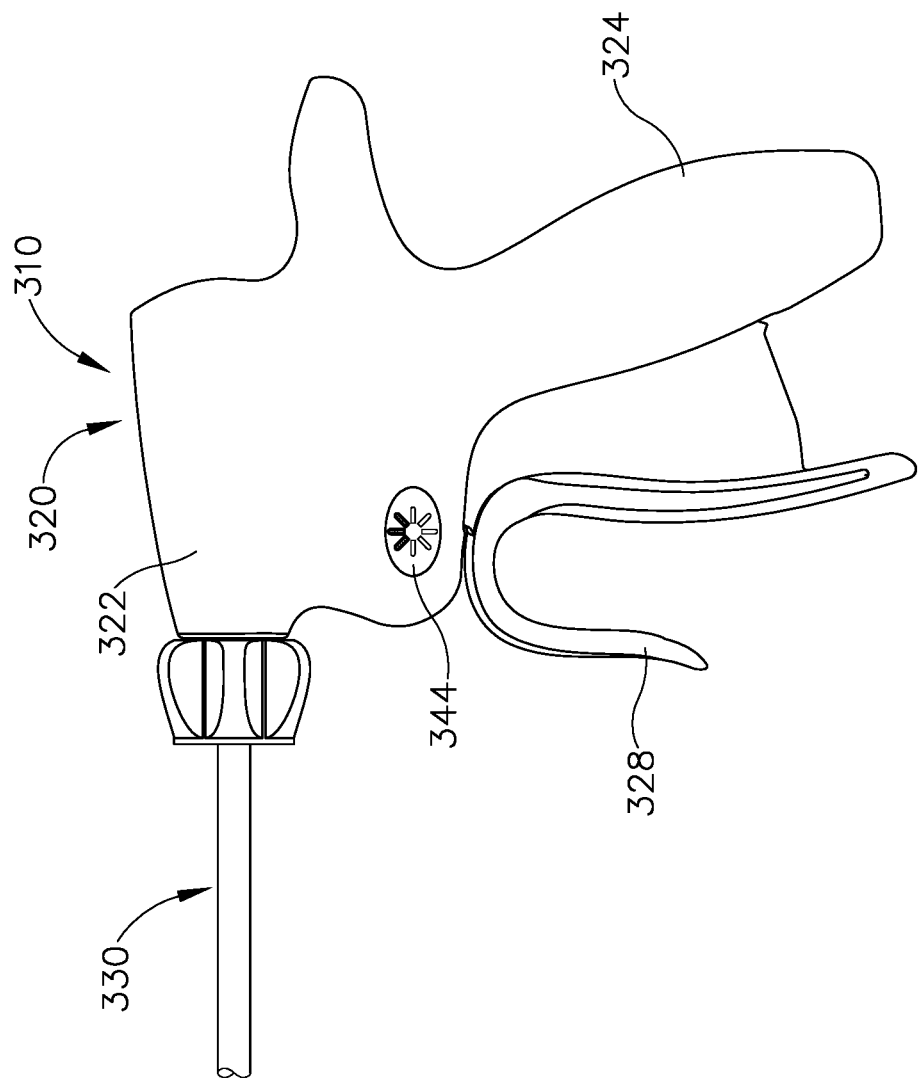
FIG. 17 depicts a side elevational view of an exemplary alternative handle assembly that is suitable for incorporation into an ultrasonic surgical instrument, showing an exemplary alert feature in an illuminated state.

In some examples, instrument (410) is configured to alert a user of the location of an activation area (444) (FIG. 18, block 506). For instance, in the example shown in FIG. 17, a portion of body (322) of instrument (310) may illuminate to alert the operator of the position of the active activation area (344). In addition or in the alternative to illumination, instrument (310) may alert an operator with one or more of sound, haptic feedback, or other suitable notification methods. In addition to alerting an operator of the location of activation area (444), in some examples, instrument (410) may be configured to alert the operator of a particular input gesture. For example, where the input gesture for a particular activation mode includes a tapping of an operator's finger or thumb, the alert may be a blinking or pulsing of light that occurs. For example, such light may blink or pulse intermittently or continuously. In examples where the input gesture includes pressing and holding, the alert may comprise a point of light that shines at a center point initially and that travels radially outwardly in all directions therefrom as it dissipates in the center. In examples where the input gesture comprises swiping or sliding, the alert may comprise progressive illumination of linearly aligned lights. Additionally or alternatively, the linearly aligned lights may blink successively to indicate a particular direction of swiping (e.g., similar to a traffic sign indicating to get into another lane). In such examples, the lights may take the form of arrows that point in a particular direction. In some examples, such illuminating alerts may include non-blinking or flashing lights. Rather, such illuminating alerts may comprise a continuously illuminated light or lights. Other suitable manners of alerting an operator will be apparent to persons skilled in the art in view of the teachings herein.

Figure 19:
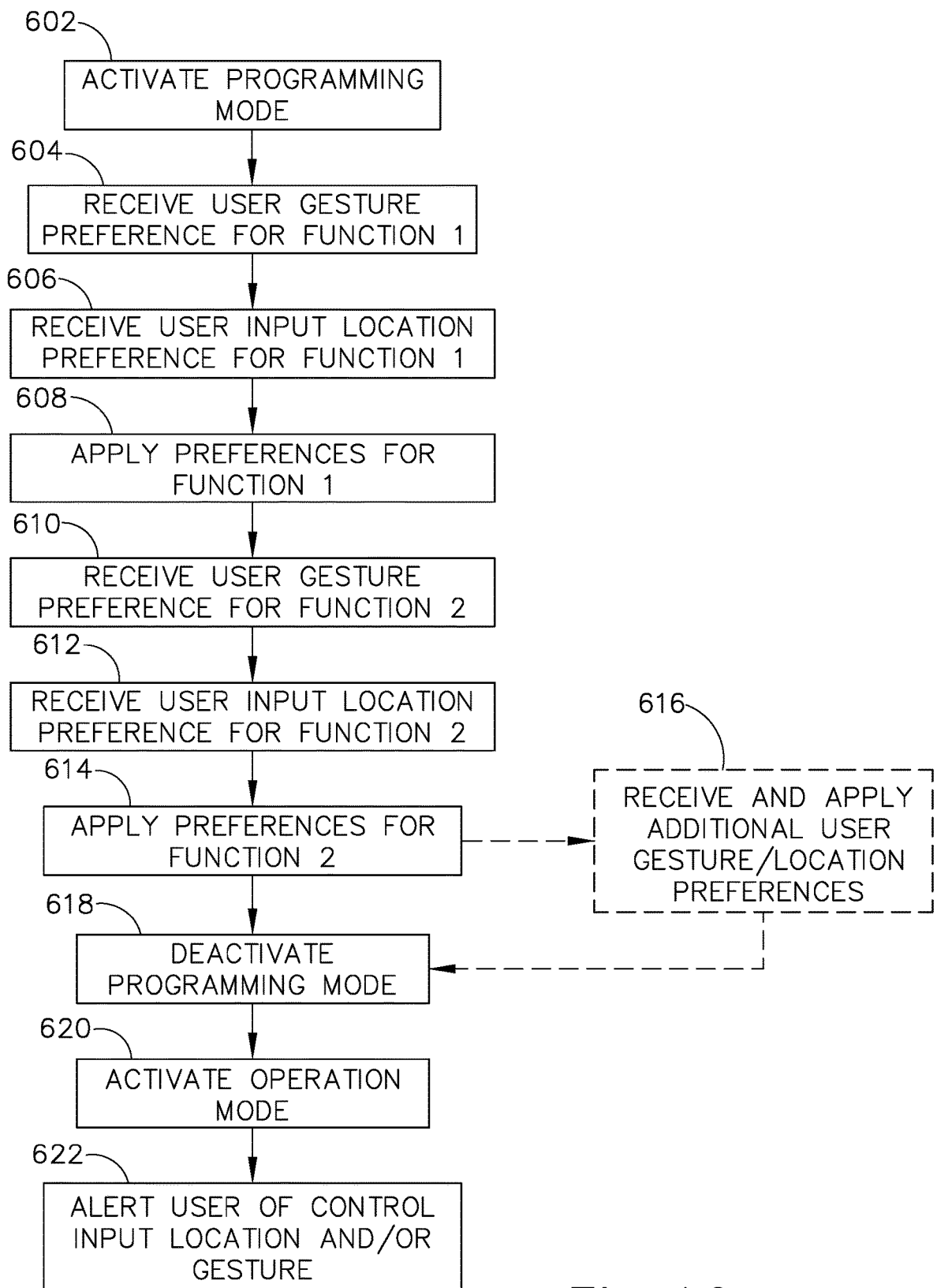
FIG. 19 depicts a flowchart showing steps of an exemplary method for changing the control scheme of a surgical instrument.

Referring to FIG. 19, instrument (410) may allow for an operator to customize or program a specific input gesture according to a specific function of instrument (410). Additionally or alternatively, instrument (410) may allow for an operator to specify a location or locations where activation area (444) should be positioned. In such examples, instrument (410) may include a programming mode (block 602) which the operator can activate at any time during use of instrument (410). In some examples, the operator may activate the programming mode (block 602) prior to utilizing instrument (410) during a surgical procedure. However, in some examples, the programming mode may be activated (block 602) during a surgical procedure in the event the operator desires to change the controls of instrument (410) during the surgical procedure. Instrument (410) may then receive the user gesture and user input location(s) preferences for a first function (blocks 604, 606) which then may be applied to instrument (410) (block 608). Next, if applicable, instrument (410) receives the user gesture and user input location(s) preferences for a second function (blocks 610, 612), which may then be applied to instrument (410) (block 614). In some instances, instrument (410) receives the user gesture and user input location(s) preferences for one or more additional functions (block 616).

In the present example, the first function may be associated with delivering a first, "minimum" ultrasonic energy level, while the second function may be associated with delivering a second, "maximum" ultrasonic energy level. However, in other examples, the first and second functions may be associated with other functions that may be performed of instrument (410) (e.g., application of RF electrosurgical energy, etc.). In the present example, the steps of receiving the user's preferences (e.g., blocks 604, 606, 610, 612) may take place with the user providing such desired gesture inputs and locations of activation areas on instrument (410) itself. For example, instrument (410) in the programming mode may prompt a user to specify the input gestures and locations. In such an example, the user may perform his or her preferred input gesture on the instrument (410). By way of example, in order to program a "proximal 2 cm swipe" as the input gesture for the first function, the user may perform such an input gesture on an aspect of instrument (410) during the programming mode. In the present example, the location of the input gesture as performed during the programming mode also serves as the activation area for such an input gesture. However, in some examples, the user may opt to select one or more different activation areas, or may opt to have the entire instrument (410), or entire portions of instrument (e.g., entire handle assembly (420)), act as an activation area.

In some examples, the steps of receiving the user's preferences (e.g., blocks 604, 606, 610, 612) may take place with the user providing such desired gesture inputs and locations of activation areas on a graphical user interface. In such examples, instrument (410) may be in communication with a user interface that allows a user to select input gesture and location preferences for one or more functions. In other examples, the user may select the particular instrument from a list on the user interface. Other suitable manners of identifying instrument (410) on interface will be apparent to persons skilled in the art in view of the teachings herein. In the examples utilizing a GUI, a user may be presented with a model or graphical representation of instrument (410) on the user interface. In some examples, user may be able to select input gestures by performing the input gesture on the model or graphical representation of the instrument on the user interface, particularly where the user interface comprises a touch screen. In other examples, the user may select from a menu of input gestures and locations of activation areas associated therewith from a predefined list, such as from a drop down menu. Other suitable methods and manners of programming particular input gestures and activation areas will be apparent to persons skilled in the art. Once the input gestures and locations of activation areas are applied, the programming mode may be deactivated (block 618) and operation mode may be activated (block 620). In some examples, the user may be alerted of the location of an activation area and/or of a particular input gesture (block 622), in a similar manner as described above with respect to block (506).

In some instances, instrument (410) may define a default input gesture for a particular function. It may be desirable to change or update such an input gesture in accordance with unifying controls of older and newer generation devices, for example. In such an event, referring to FIG. 20, instrument (410) may be switched to a programming mode (block 702) and then connected to a centralized system (block 704). The system may investigate and determine whether settings of instrument (410), such as particular input gesture(s) are the most recent input gestures programmed onto instrument (410) (blocks 706, 708). If such settings are up to date the system ends the investigation (block 710). However, if the settings are not up to date, the system may prompt a user with the option of updating the settings to the most up to date settings (block 712), or to maintain the current settings. If the user declines to updates the settings, the process ends (block 710). However, if the user desires to updates the settings, the system updates the settings with the most up to date settings, such as the most up to date input gesture(s).

Figure 20:
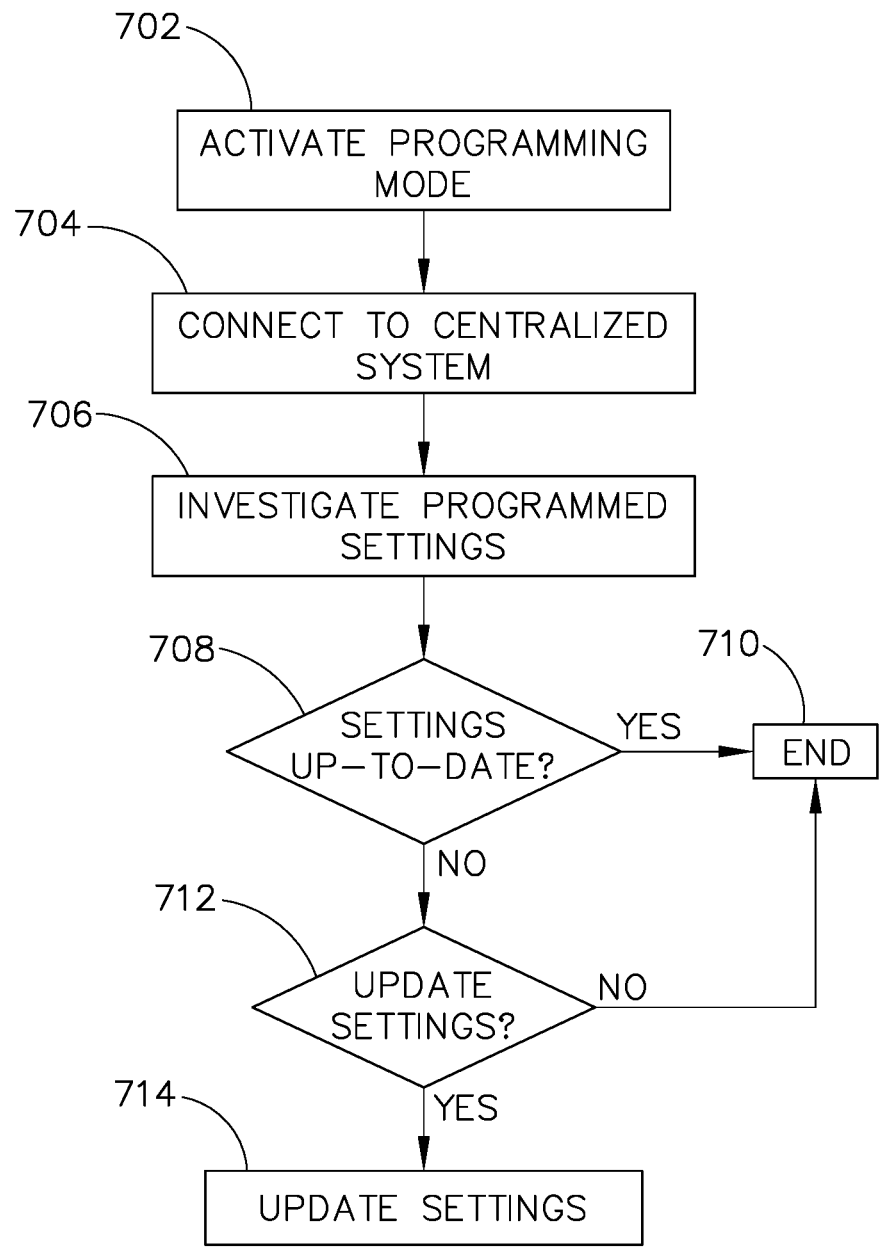
FIG. 20 depicts a flowchart showing steps of an exemplary method for updating control settings of a surgical instrument.

It will be understood that some or all of the steps of the methods described herein, such as those shown in FIGS. 18, 19, and 20 may be incorporated into any of the methods described herein, such as those embodied in flowcharts of FIGS. 18, 19, and 20, or into other suitable or appropriate methods. Moreover, while the foregoing teachings have been described with respect to particular examples of instruments (e.g., instruments (10, 110, 210, 310, 410)), it will be understood that such teachings may be performed with respect to, or incorporated into other instruments described herein, or other suitable instruments.

It will be further understood that using activation areas comprising sensors (245) in order to activate instruments, such as those described herein, instead of using mechanical parts such as buttons, may increase reliability and durability for reusable devices. Moreover, the physical continuity of body (222) that comes with a lesser amount of moving parts allows for easier cleaning and prevents fluid and debris from ingressing into internal portions of instrument (210) during use and during sterilization. Furthermore, there are a variety of sensors that may be utilized in particular instruments. For example, sensors that are programmable (e.g., as described above) could be utilized in some instruments, while more limited capability sensors that may only perform a single or a few functions may be utilized in other instances, such as in more cost sensitive situations. Moreover, while a sensor or sensors may be applied to an entire instrument, thus making an entire instrument an activation area, it is also possible to strategically place such sensor(s) on smaller regions or portions of instruments. Moreover, such sensors, particularly projected capacitance sensors, can assume a variety of characteristics depending on the substrate to which it is bonded. For example, such sensors may be applied to substrates including, but not limited to, plastic film, glass, and others; and can also be over-molded and formed onto substrates. Other suitable methods of incorporating such sensors onto substrates and into or onto instruments will be apparent to persons skilled in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a gripping assembly defining a first opening for receiving a finger or a thumb of a user, wherein the gripping assembly comprises a first deformable feature, wherein the first deformable feature is configured to be moved in order to increase or decrease a cross-sectional area of the first opening; (b) a shaft assembly extending distally from the gripping assembly; (c) an end effector, wherein the end effector is positioned at a distal end of the shaft assembly, wherein the end effector comprises a first member; and (d) a pivoting member, wherein the pivoting member is pivotably coupled with the shaft assembly, wherein the pivoting member is pivotable with respect to the first member of the end effector between an open position and a closed position to thereby clamp tissue between the first member and the pivoting member.

Example 2

The surgical instrument of Example 1, wherein the gripping assembly defines a second opening for receiving another finger or thumb of the user, wherein the gripping assembly comprises a second deformable feature, wherein the second deformable feature is configured to be moved in order to increase or decrease a cross-sectional area of the second opening.

Example 3

The surgical instrument of any one or more of Examples 1 through 2, wherein the first deformable feature comprises a malleable member.

Example 4

The surgical instrument of any one or more of Examples 1 through 3, wherein the first deformable feature comprises a plurality of movable linkages.

Example 5

The surgical instrument of any one or more of Examples 1 through 4, wherein the gripping assembly and the pivoting member cooperate to provide a scissor grip configuration.

Example 6

The surgical instrument of any one or more of Examples 1 through 5, wherein the first opening includes a tapered portion.

Example 7

The surgical instrument of any one or more of Examples 1 through 6, wherein the first member of the end effector comprises an ultrasonic blade.

Example 8

The surgical instrument of Example 7, wherein the pivoting member comprises a clamp arm including a clamp pad, Example the clamp arm is member is pivotable with respect to the blade to thereby clamp tissue between the ultrasonic blade and the clamp pad.

Example 9

The surgical instrument of Example 8, further comprising a movable sheath configured to selectively envelop a portion of the ultrasonic blade.

Example 10

The surgical instrument of Example 9, wherein the gripping member further comprises an actuating member, wherein the sheath is configured to move relative to the ultrasonic blade in response to actuation of the actuating member.

Example 11

The surgical instrument of any one or more of Examples 9 through 10, wherein the sheath is slidable between a proximal position and a distal position along the ultrasonic blade, wherein the sheath in the distal position is configured to increase the effective cross sectional area of a distal portion of the end effector.

Example 12

The surgical instrument of any one or more of Examples 9 through 11, wherein the sheath comprises a textured outer surface.

Example 13

The surgical instrument of Example 12, wherein the textured outer surface comprises knurling.

Example 14

The surgical instrument of any one or more of Examples 7 through 13, further comprising an ultrasonic transducer assembly, wherein the ultrasonic transducer assembly is in acoustic communication with the ultrasonic blade.

Example 15

The surgical instrument of Example 14, wherein the ultrasonic transducer assembly is integral with at least part of the gripping portion.

Example 16

A surgical instrument comprising: (a) a body; (b) a shaft assembly extending distally from the body; (c) an end effector at a distal end of the shaft assembly, wherein the end effector comprises: (i) a first member, and (ii) a second member, wherein the second member is pivotable relative to the first member from an open position to a closed position to thereby clamp tissue between the first member and the second member, wherein the end effector defines a first cross sectional area when the second member is in the closed position; and (d) a sheath movable between a first position and a second position relative to the end effector, wherein the end effector defines a second cross sectional area when the sheath is in the second position and the second member is in the closed position.

Example 17

A surgical instrument comprising: (a) a body; (b) a shaft assembly extending distally from the body; (c) an end effector at a distal end of the shaft assembly, wherein the end effector has an active element; and (d) a touch sensitive activation area positioned on at least one of the body or the shaft assembly, wherein the touch sensitive activation area comprises a sensor configured to receive a touch input, wherein the touch sensitive activation area is configured to activate the active element of the end effector in response to the sensor receiving a touch input.

Example 18

The surgical instrument of Example 17, wherein the sensor comprises a projected capacitive sensor.

Example 19

The surgical instrument of any one or more of Examples 17 through 18, wherein the touch sensitive activation area is movable based on a position of the body and/or the shaft assembly.

Example 20

The surgical instrument of any one or more of Examples 17 through 19, wherein a position of the touch sensitive activation area is movable based on an input from a user.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly extending distally from the body;
   (c) an end effector at a distal end of the shaft assembly, wherein the end effector has an active element;
   (d) a touch sensitive activation area positioned on at least one of the body or the shaft assembly, wherein the touch sensitive activation area comprises a sensor configured to receive a first touch input, wherein the touch sensitive activation area is configured to activate the active element of the end effector in response to the sensor receiving the first touch input; and
   (e) a second touch sensitive activation area positioned on at least one of the body or the shaft assembly, wherein the second touch sensitive activation area comprises a second sensor configured to receive a second touch input, wherein the second touch sensitive activation area is configured to activate the active element of the end effector in response to the second sensor receiving a second touch input.

2. The surgical instrument of claim 1, wherein the sensor comprises a projected capacitive sensor.

3. The surgical instrument of claim 1, wherein the touch sensitive activation area is movable based on a position of at least one of the body or the shaft assembly.

4. The surgical instrument of claim 1, wherein a position of the touch sensitive activation area is movable based on a grasping input from a user.

5. The surgical instrument of claim 4, wherein the signal is configured to activate a power level at which the active element of the end effector operates in response to the sensor receiving the touch input.

6. The surgical instrument of claim 1, wherein the sensor comprises a film.

7. The surgical instrument of claim 6, wherein the film comprises a capacitive touch sensitive film.

8. The surgical instrument of claim 7, further comprising a circuit board in communication with the capacitive touch sensitive film, wherein the circuit board is configured to activate the active element of the end effector in response to the sensor receiving the first touch input.

9. The surgical instrument of claim 1, wherein the first touch input is a plurality of taps input, and wherein the touch sensitive activation area is configured to activate the active element of the end effector in response to the sensor receiving the plurality of taps input.

10. The surgical instrument of claim 1, wherein the first touch input is a slide input, and wherein the touch sensitive activation area is configured to activate the active element of the end effector in response to the sensor receiving the slide input.

11. The surgical instrument of claim 1, wherein the first touch input is the same as the second touch input.

12. The surgical instrument of claim 1, wherein the second touch input is different than the first touch input.

13. The surgical instrument of claim 1, wherein the touch sensitive activation area is configured to change a power level at which the active element of the end effector operates in response to the sensor receiving a second touch input.

14. The surgical instrument of claim 1, further comprising a second sensor configured to generate a signal in response to the orientation of the surgical instrument.

15. The surgical instrument of claim 14, wherein the signal is configured to activate a first specific area of the touch sensitive activation area.

16. The surgical instrument of claim 15, wherein the signal is configured to deactivate a second specific area of the touch sensitive activation area.

17. A surgical instrument, comprising:
(a) a body;
(b) a shaft assembly extending distally from the body;
(c) an end effector extending distally from the shaft assembly, wherein the end effector has an active element;
(d) a touch sensitive activation area positioned on at least one of the body or the shaft assembly, wherein the touch sensitive activation area comprises a first sensor configured to receive a touch input, wherein the touch sensitive activation area is configured to activate the active element of the end effector in response to the sensor receiving the touch input;
(e) a second sensor configured to determine an orientation of the body, wherein the second sensor is configured to alter the touch sensitive activation area in response to a determined orientation of the body.

18. A surgical instrument, comprising:
(a) a body;
(b) a shaft assembly extending distally from the body;
(c) an end effector extending distally from the shaft assembly, wherein the end effector has an active element; and
(d) a touch sensitive activation area positioned on at least one of the body or the shaft assembly, wherein the touch sensitive activation area is configured to identify a specific touch input, wherein the touch sensitive activation area is configured to activate the active element of the end effector in response to receiving the specific touch input, wherein the touch sensitive activation area is configured to illuminate to identify the specific touch input necessary to activate the active element.

* * * * *